United States Patent
Moubarak et al.

(10) Patent No.: US 12,419,638 B1
(45) Date of Patent: Sep. 23, 2025

(54) ADAPTIVE KNIFE-BASED CLOSURE METHODS FOR SURGICAL STAPLER

(71) Applicant: Cilag GmbH International, Zug (CH)

(72) Inventors: Paul Moubarak, West Chester, OH (US); Christopher M. Korte, North Bend, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/752,932

(22) Filed: Jun. 25, 2024

(51) Int. Cl.
| | |
|---|---|
| *A61B 17/072* | (2006.01) |
| *A61B 17/068* | (2006.01) |
| *A61B 34/30* | (2016.01) |
| *A61B 90/00* | (2016.01) |
| *A61B 17/00* | (2006.01) |

(Continued)

(52) U.S. Cl.
CPC ...... *A61B 17/07207* (2013.01); *A61B 17/068* (2013.01); *A61B 17/072* (2013.01); *A61B 34/30* (2016.02); *A61B 90/06* (2016.02); *A61B 2017/00022* (2013.01); *A61B 2017/00234* (2013.01); *A61B 2017/00398* (2013.01); *A61B 2017/07285* (2013.01);

(Continued)

(58) Field of Classification Search
CPC . A61B 17/068; A61B 17/0686; A61B 17/072; A61B 17/07207; A61B 17/115; A61B 17/00234; A61B 17/320092; A61B 34/30; A61B 34/37; A61B 34/71; A61B 2017/00022; A61B 2017/00398; A61B 2017/00477; A61B 2017/07214; A61B 2017/07285; A61B 90/06

USPC .............. 227/19, 175.2, 175.1, 176.1, 180.1; 606/1, 130, 139, 169, 208, 219
See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |

(Continued)

FOREIGN PATENT DOCUMENTS

| | | |
|---|---|---|
| EP | 2992841 A2 | 3/2016 |
| EP | 3412225 A1 | 12/2018 |

(Continued)

OTHER PUBLICATIONS

U.S. Appl. No. 62/868,457, entitled "Surgical Systems with Multiple RFID Tags," filed Jun. 28, 2019.

(Continued)

*Primary Examiner* — Scott A Smith
(74) *Attorney, Agent, or Firm* — Frost Brown Todd LLP

(57) ABSTRACT

An apparatus (1000) includes an end effector (200), a motor (1100), a sensor (1104), and a controller (1150). The end effector includes first and second jaws (202, 204) and a knife (206). The controller obtains using the sensor a first force value exerted by the motor as the knife is contacting the ramp surface. The controller determines whether the first force value exerted by the motor exceeds a first predetermined force threshold as the knife is contacting the ramp surface. The controller is configured to alter travel of the knife. Altering the travel of the knife includes at least one of: pausing the knife for a predetermined amount of time, pausing the knife until a second force value exerted by the motor obtained from the sensor is below the first predetermined force threshold, or advancing the knife at a second speed that is less than the first speed.

20 Claims, 21 Drawing Sheets

(51) Int. Cl.
*A61B 17/32* (2006.01)
*A61B 34/00* (2016.01)

(52) U.S. Cl.
CPC ....... *A61B 17/320092* (2013.01); *A61B 34/71* (2016.02); *A61B 2090/066* (2016.02)

(56) References Cited

U.S. PATENT DOCUMENTS

| | | | |
|---|---|---|---|
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 6,063,098 | A * | 5/2000 | Houser .......... A61B 17/320092 606/169 |
| 6,443,973 | B1 | 9/2002 | Whitman |
| 7,793,812 | B2 | 9/2010 | Moore et al. |
| 7,810,692 | B2 | 10/2010 | Hall et al. |
| 7,922,063 | B2 | 4/2011 | Zemlok et al. |
| 8,012,170 | B2 | 9/2011 | Whitman et al. |
| 8,028,885 | B2 | 10/2011 | Smith et al. |
| 8,210,413 | B2 | 7/2012 | Whitman et al. |
| 8,241,322 | B2 * | 8/2012 | Whitman .............. A61B 17/068 606/208 |
| 8,292,150 | B2 | 10/2012 | Bryant |
| 8,342,378 | B2 | 1/2013 | Marczyk et al. |
| 8,910,847 | B2 | 12/2014 | Nalagatla et al. |
| 8,989,903 | B2 | 3/2015 | Weir et al. |
| 9,226,750 | B2 | 1/2016 | Weir et al. |
| 9,445,816 | B2 | 9/2016 | Swayze et al. |
| 9,463,022 | B2 | 10/2016 | Swayze et al. |
| 9,532,783 | B2 | 1/2017 | Swayze et al. |
| 9,597,081 | B2 | 3/2017 | Swayze et al. |
| 9,801,626 | B2 | 10/2017 | Parihar et al. |
| 9,808,307 | B2 | 11/2017 | Trees et al. |
| 9,814,530 | B2 | 11/2017 | Weir et al. |
| 9,826,976 | B2 | 11/2017 | Parihar et al. |
| 9,844,368 | B2 | 12/2017 | Boudreaux et al. |
| 9,867,612 | B2 | 1/2018 | Parihar et al. |
| 10,045,780 | B2 | 8/2018 | Adams et al. |
| 10,307,157 | B2 | 6/2019 | Miller et al. |
| 10,702,266 | B2 | 7/2020 | Parihar et al. |
| 10,888,318 | B2 | 1/2021 | Parihar et al. |
| 11,123,074 | B2 | 9/2021 | Adams et al. |
| 11,185,324 | B2 | 11/2021 | Adams et al. |
| 11,185,331 | B2 | 11/2021 | Adams et al. |
| 11,317,917 | B2 * | 5/2022 | Shelton, IV ......... A61B 17/072 |
| 11,395,652 | B2 | 7/2022 | Parihar et al. |
| 11,406,381 | B2 | 8/2022 | Parihar et al. |
| 11,464,516 | B2 | 10/2022 | Adams et al. |
| 11,564,679 | B2 | 1/2023 | Parihar et al. |
| 11,690,615 | B2 | 7/2023 | Parihar et al. |
| 11,883,024 | B2 * | 1/2024 | Bakos ............ A61B 17/320092 |
| 12,239,318 | B2 * | 3/2025 | Hibner ................ A61B 17/068 |
| 12,279,845 | B2 * | 4/2025 | Moubarak .............. A61B 34/71 |
| 2007/0175951 | A1 | 8/2007 | Shelton et al. |
| 2008/0185419 | A1 | 8/2008 | Smith et al. |
| 2009/0101692 | A1 | 4/2009 | Whitman et al. |
| 2009/0108048 | A1 | 4/2009 | Zemlok et al. |
| 2009/0206135 | A1 | 8/2009 | Hall et al. |
| 2010/0320252 | A1 * | 12/2010 | Viola .................. A61B 17/068 227/176.1 |
| 2011/0174099 | A1 | 7/2011 | Ross et al. |
| 2013/0110088 | A1 | 5/2013 | Wenchell |
| 2013/0214025 | A1 | 8/2013 | Zemlok et al. |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2015/0313676 | A1 * | 11/2015 | Deodhar ................. A61B 34/30 606/130 |
| 2016/0270780 | A1 | 9/2016 | Hall et al. |
| 2017/0258471 | A1 | 9/2017 | DiNardo et al. |
| 2018/0360452 | A1 | 12/2018 | Shelton, IV et al. |
| 2018/0368836 | A1 | 12/2018 | Auld et al. |
| 2019/0059888 | A1 | 2/2019 | Shelton, IV et al. |
| 2019/0380735 | A1 * | 12/2019 | Cuti ............... A61B 17/320092 |
| 2020/0305868 | A1 * | 10/2020 | Shelton, IV ......... A61B 17/072 |
| 2022/0031350 | A1 * | 2/2022 | Witte ............... A61B 17/07207 |
| 2023/0320726 | A1 | 10/2023 | Parihar et al. |

FOREIGN PATENT DOCUMENTS

| | | |
|---|---|---|
| EP | 3545862 A2 | 10/2019 |
| WO | WO 2018/234883 A1 | 12/2018 |
| WO | WO 2019/043507 A1 | 3/2019 |
| WO | WO 2019/130087 A1 | 7/2019 |

OTHER PUBLICATIONS

U.S. Appl. No. 18/588,684, entitled "Methods of Surgical Stapling," filed Feb. 27, 2024.

* cited by examiner

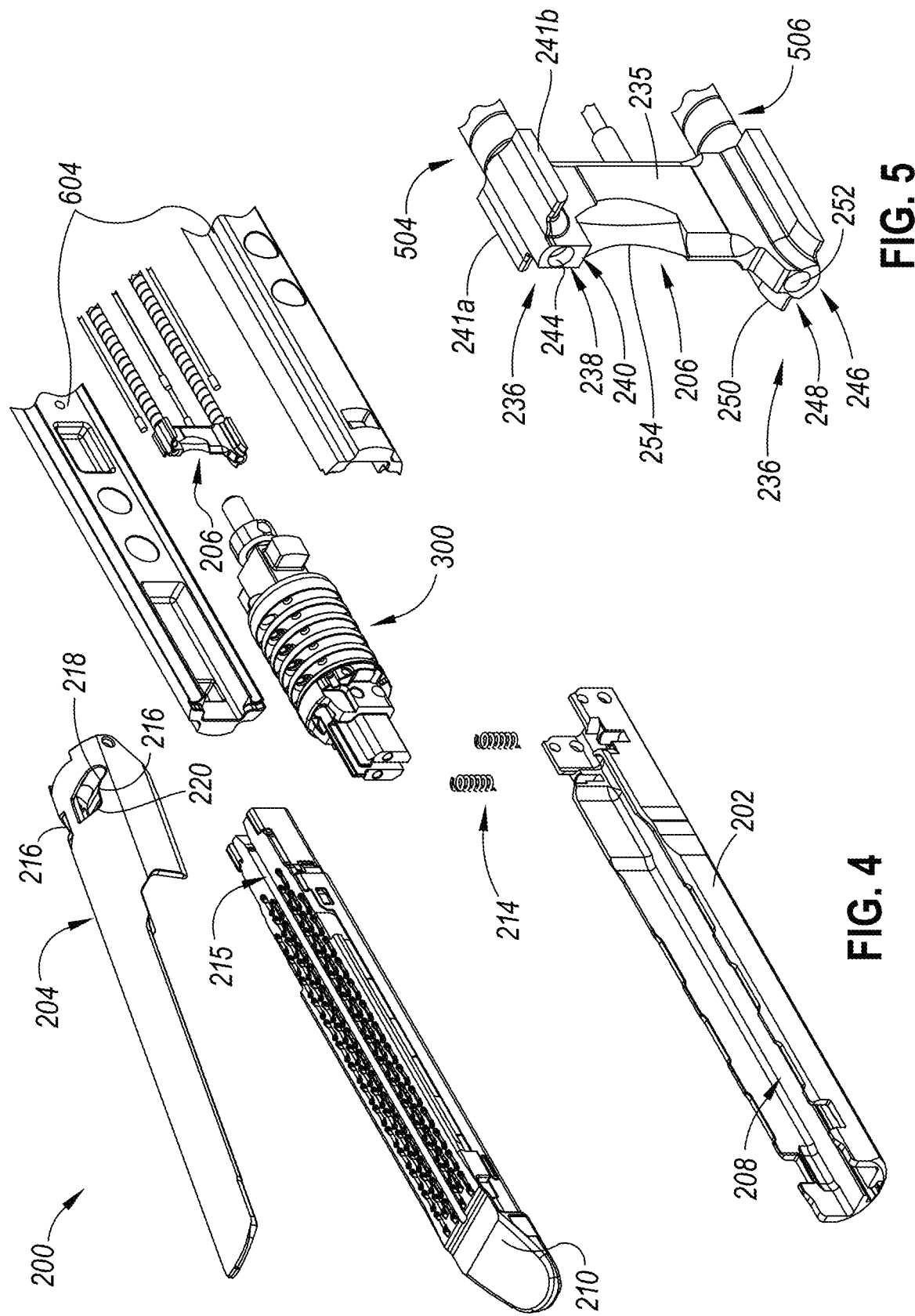

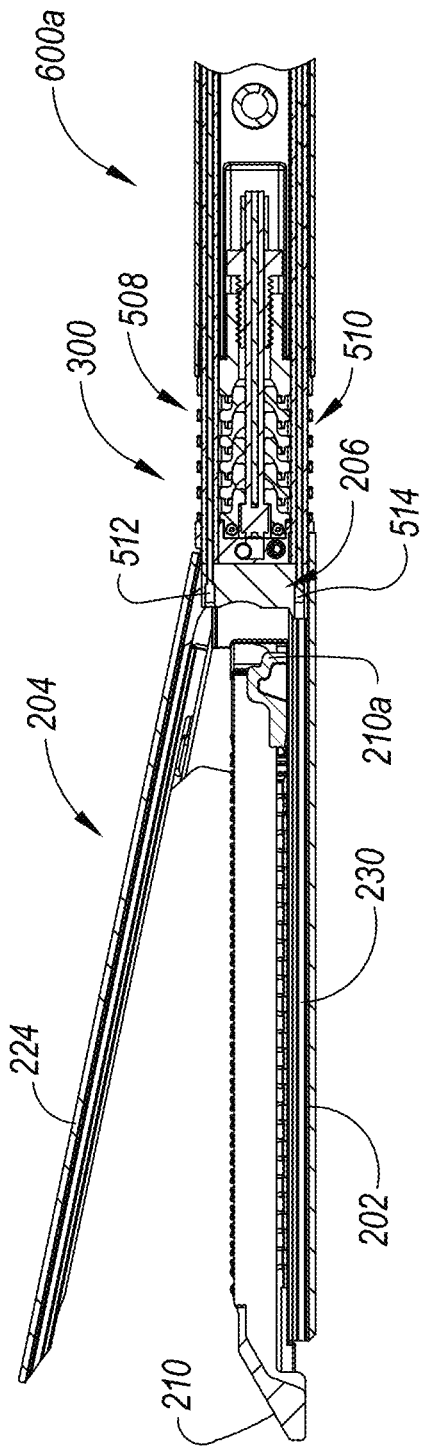
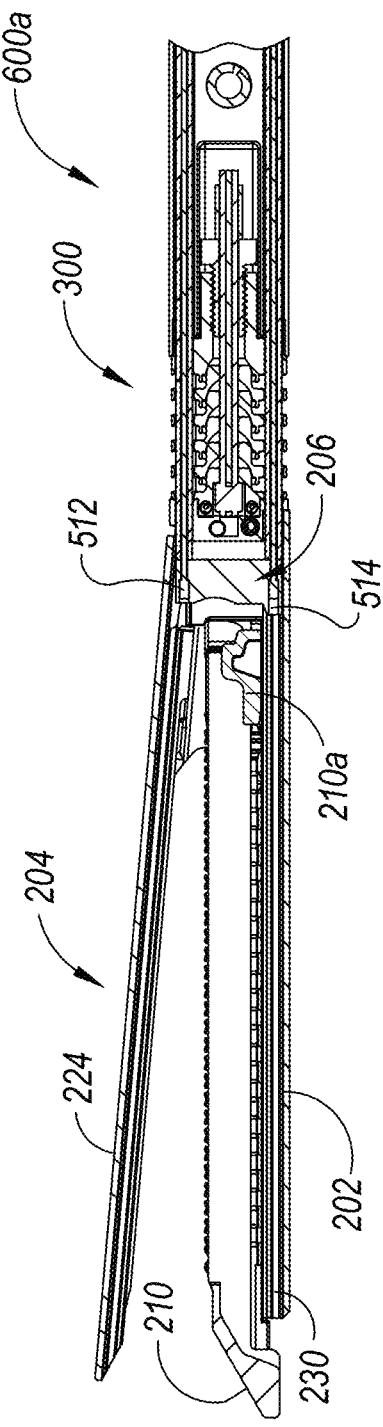
FIG. 8A
FIG. 8B

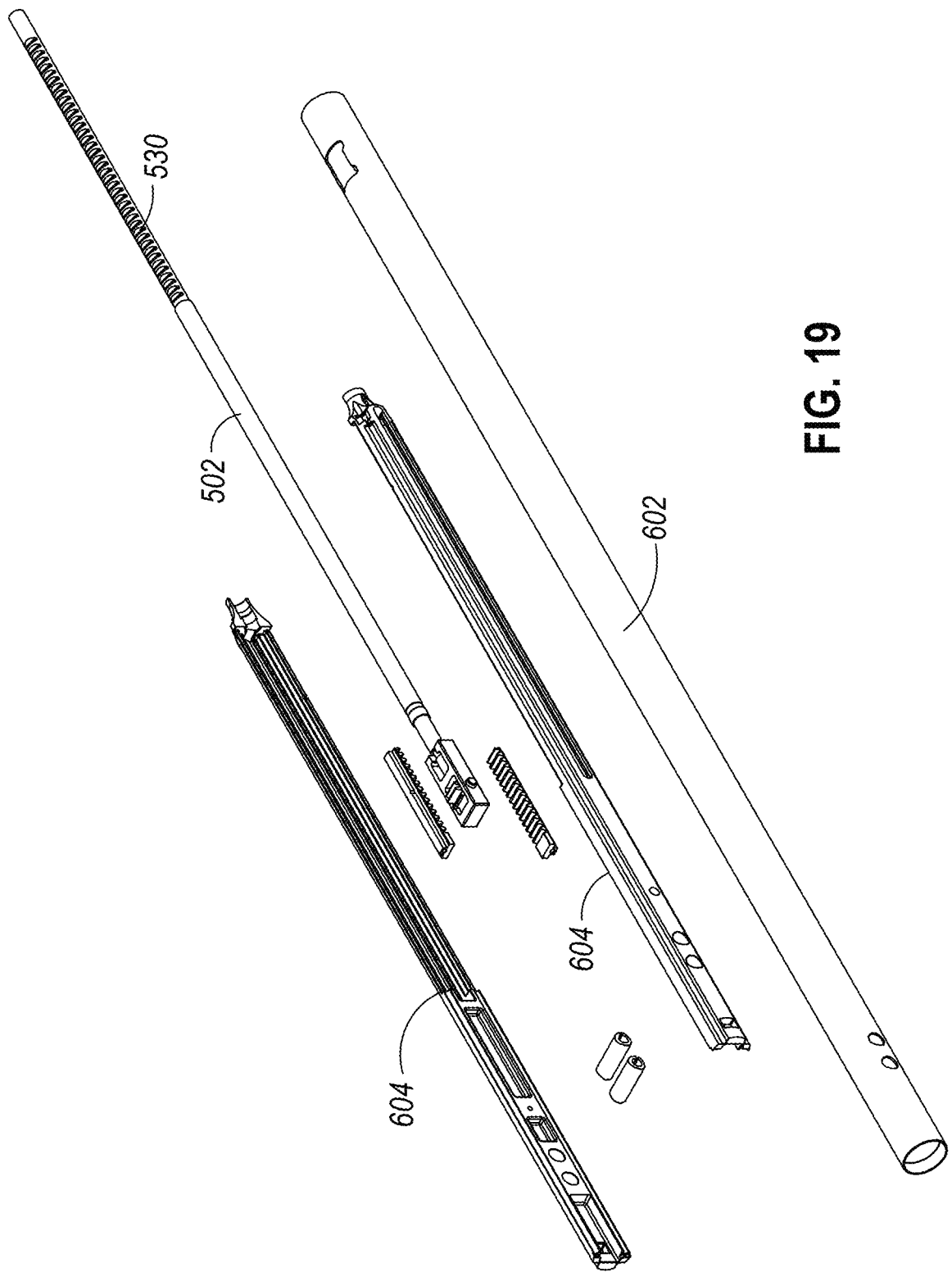

ADAPTIVE KNIFE-BASED CLOSURE METHODS FOR SURGICAL STAPLER

BACKGROUND

In some settings, endoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle portion that is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

It is desirable to reduce the force spikes encountered by a surgical instrument drivetrain during a surgical procedure. While various kinds of surgical staplers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate examples of the invention, and, together with the general description of the invention given above, and the detailed description of the examples given below, serve to explain the principles of the present invention.

FIG. 4 is an exploded view of a distal end portion of the surgical instrument of FIG. 1;

FIG. 5 is an enlarged perspective view of a knife of the end effector of the surgical instrument of FIG. 1;

FIG. 8A is a side cross-sectional view of a distal end portion of the surgical instrument of FIG. 1, depicting the anvil in an open position;

FIG. 8B is a side cross-sectional view of the distal end portion of the surgical instrument of FIG. 1, depicting the anvil in a grasping position with the knife partially advanced;

FIG. 19 is a perspective view of a shaft assembly, a differential, and a firing rod of the surgical instrument of FIG. 1.

DETAILED DESCRIPTION

Figure 1:
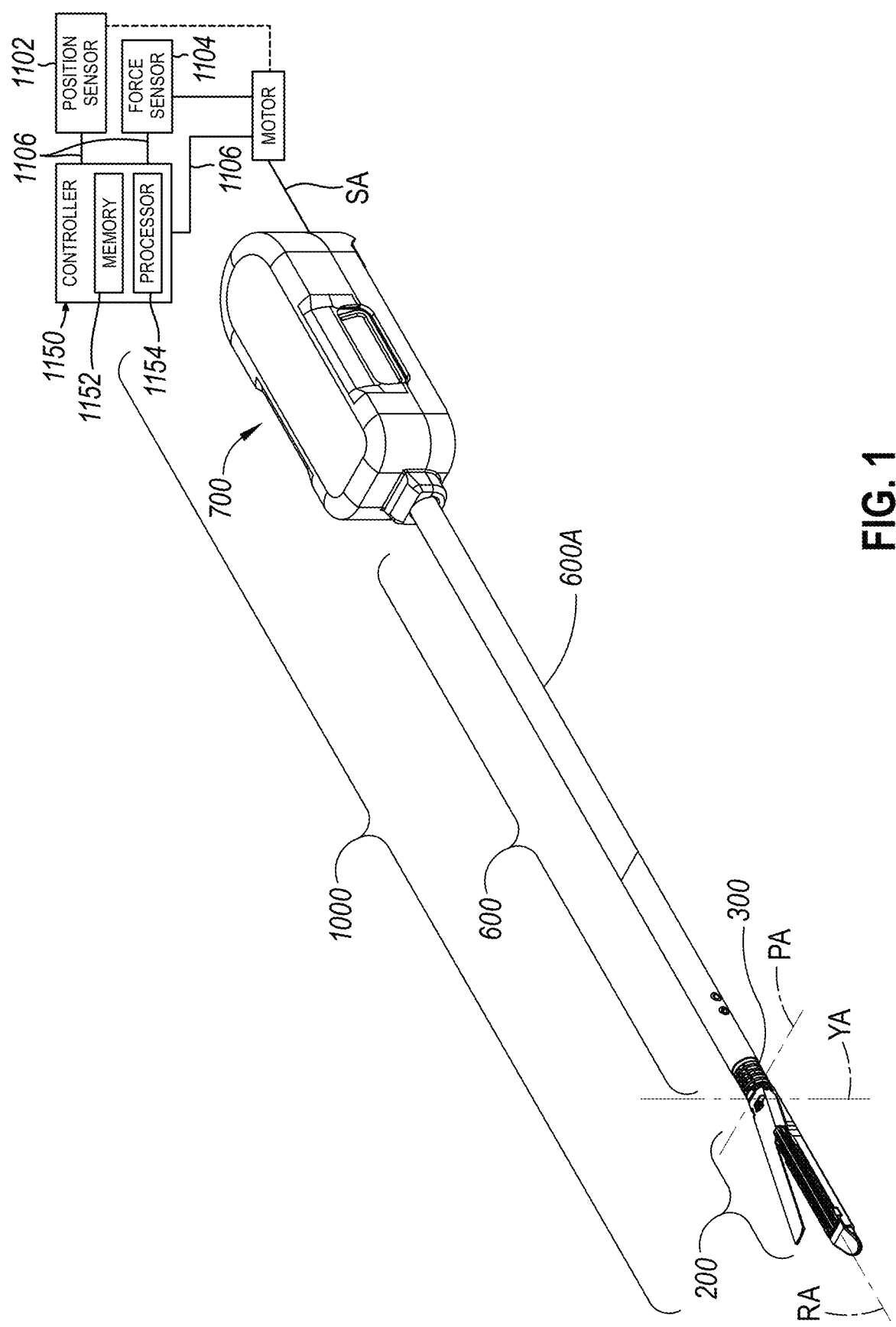
FIG. 1 is a perspective view of an illustrative surgical instrument having a housing, a shaft assembly, an articulation joint, an end effector, a motor, sensors, and a controller.

The following detailed description should be read with reference to the drawings, in which like elements in different drawings are identically numbered. The drawings, which are not necessarily to scale, depict selected versions and are not intended to limit the scope of the invention. The detailed description illustrates by way of example, not by way of limitation, the principles of the invention. This description will clearly enable one skilled in the art to make and use the invention, and describes several versions, adaptations, variations, alternatives and uses of the invention, including what is presently believed to be the best mode of carrying out the invention.

Numerous specific details are set forth to provide a thorough understanding of the overall structure, function, manufacture, and use of the versions as described in the specification and illustrated in the accompanying drawings. Well-known operations, components, and elements have not been described in detail so as not to obscure the versions described in the specification. The reader will understand that the versions described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures, and "substantially equal" values encompass nominally equal values.

Furthermore, the use of "couple", "coupled", or similar phrases should not be construed as being limited to a certain number of components or a particular order of components unless the context clearly dictates otherwise.

I. OVERVIEW OF ILLUSTRATIVE SURGICAL INSTRUMENT

Figure 2:
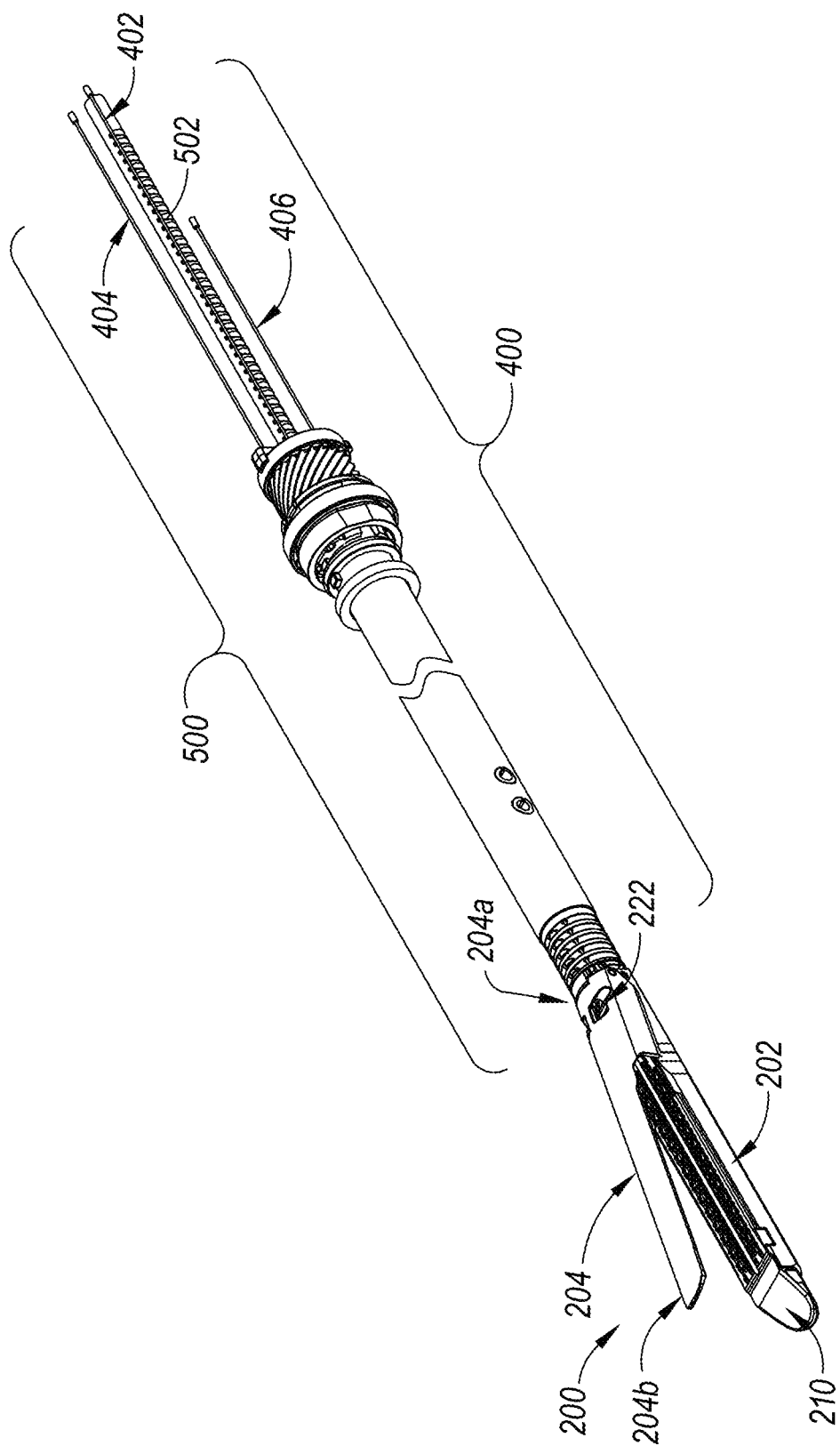
FIG. 2 is a partial perspective view of the surgical instrument of FIG. 1, with select components omitted from view to reveal portions of a cable articulation subsystem, a knife firing subsystem, and a roll subsystem of the surgical instrument.

FIGS. 1-2 show an illustrative surgical instrument 1000 that is configured to grasp, clamp, incise, and seal patient tissue with staples. The surgical instrument 1000 comprises an end effector 200, an articulation joint 300 (also referred to as a "continuum joint"), an articulation drive subsystem 400 configured to articulate the end effector 200 via the articulation joint 300, a knife firing subsystem 500 configured to actuate the end effector 200 between various positions (e.g., an open position, a grasping position, and a clamping position) and to incise and staple patient tissue, a roll subsystem 600 configured to rotate the end effector 200 about a roll axis RA, and a housing 700.

As shown in FIG. 1, the surgical instrument 1000 additionally includes at least one motor (shown as motor 1100), a plurality of sensors (shown as including a position sensor 1102 and a force sensor 1104) and a controller 1150. The controller 1150 includes a memory 1152 and a processor 1154. The controller 1150 may include a counter, or alternatively, a separate counter may be incorporated separate from the controller 1150. As shown, the controller 1150 is in communication with the motor 1100, the position sensor 1102, and the force sensor 1104 using wires 1106. The force sensor 1104 provides power to the knife firing subsystem 500. The force sensor 1104 is configured to sense the force exerted by the motor 1100 on the knife firing subsystem 500. The position sensor 1102 may optionally be in communication with the motor 1100. In some versions, the force sensor 1104 comprises a torque sensor (such as a load cell) configured to sense torque of the motor 1100. The force sensor 1104 may be colinear with the shaft axis (SA).

With reference to FIG. 1-2, the shaft assembly 600A extends proximally from the end effector 200 along a shaft axis SA. The housing 700 extends proximally from the shaft assembly 600A. The motor 1100, the position sensor 1102, and the force sensor 1104 are sized and configured to be positioned within the housing 700. The motor 1100 is coaxially positioned along the shaft axis SA. The motor 1100 is configured to actuate a knife 206 along a firing stroke using the knife firing subsystem 500 while the staple cartridge 210 is housed within the first jaw 202 to thereby cut tissue clamped by the first and second jaws 202, 204.

Figure 3:
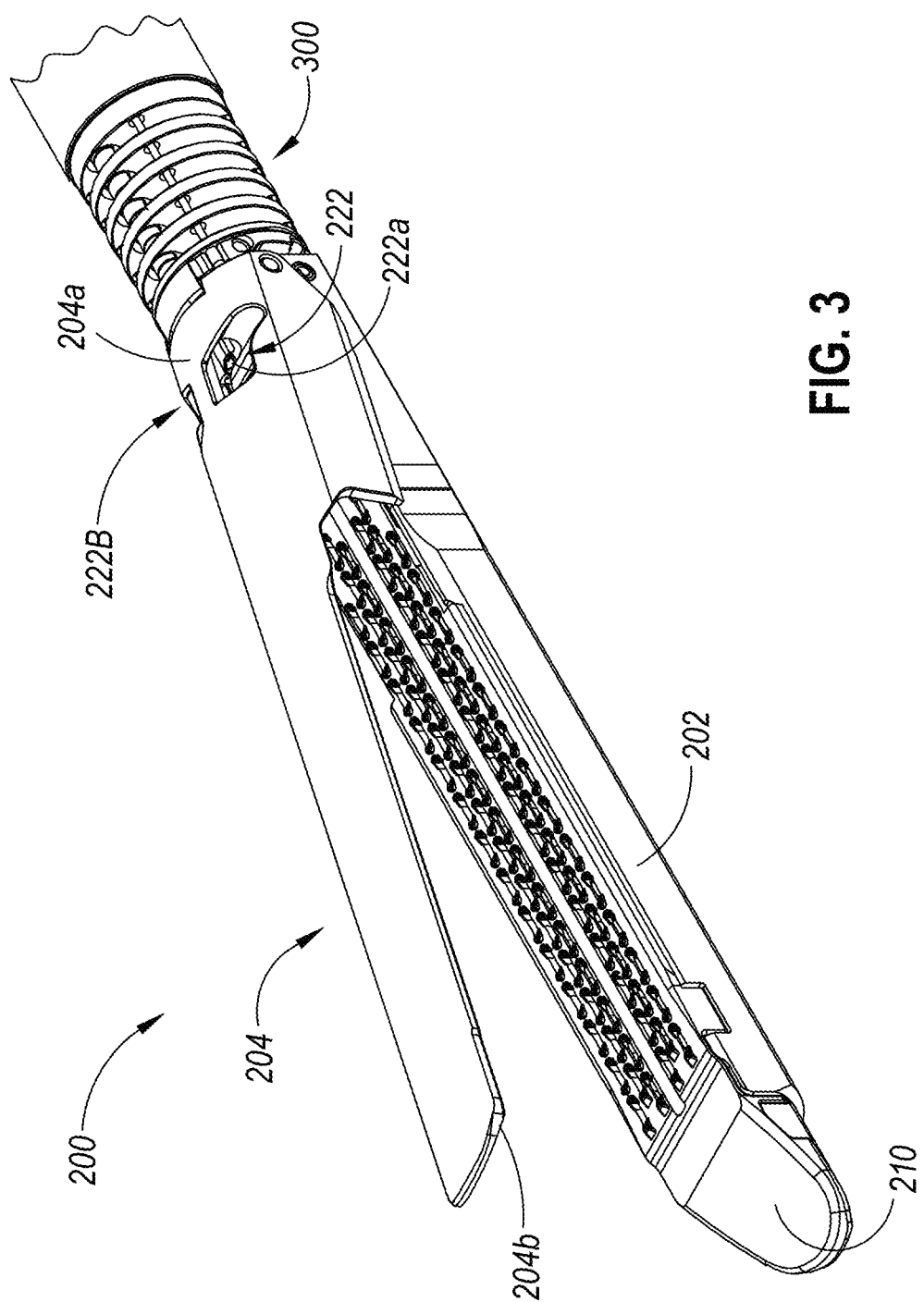
FIG. 3 is an enlarged perspective view of the end effector and the articulation joint of the surgical instrument of FIG. 1.

As shown best in FIGS. 3-4, the end effector 200 comprises a first jaw 202 (also known as a "cartridge jaw" or a "channel") and a second jaw 204 (also known as an "anvil jaw" or just "anvil") movable relative to the cartridge jaw 202 between an open position and a closed position. The cartridge jaw 202 and anvil jaw 204 may be elongated in form. The cartridge jaw 202 defines an elongated channel 208 for receiving a staple cartridge 210 (also known as a "reload"). The end effector 200 is operable to clamp, staple, and cut tissue. The end effector 200 includes the first jaw 202, the second jaw 204, and the knife 206. The first jaw 202 is configured to selectively receive a staple cartridge 210. The second jaw 204 includes a plurality of staple forming pockets 211 (see FIG. 9A).

At least one of the first or second jaws 202, 204 includes a ramp surface 216. As shown in FIGS. 4 and 9A-9D, the second jaw 204 includes the ramp surface 216. The ramp surface 216 is integrally formed together as a unitary piece together with the second jaw 204. Alternatively, the ramp surface 216 may be separately formed from the second jaw 204 and subsequently coupled with the second jaw 204. The ramp surface 216 includes a concave portion 258 and a convex portion 260. As shown, the concave portion 258 is proximal to the convex portion 260.

Figure 7:
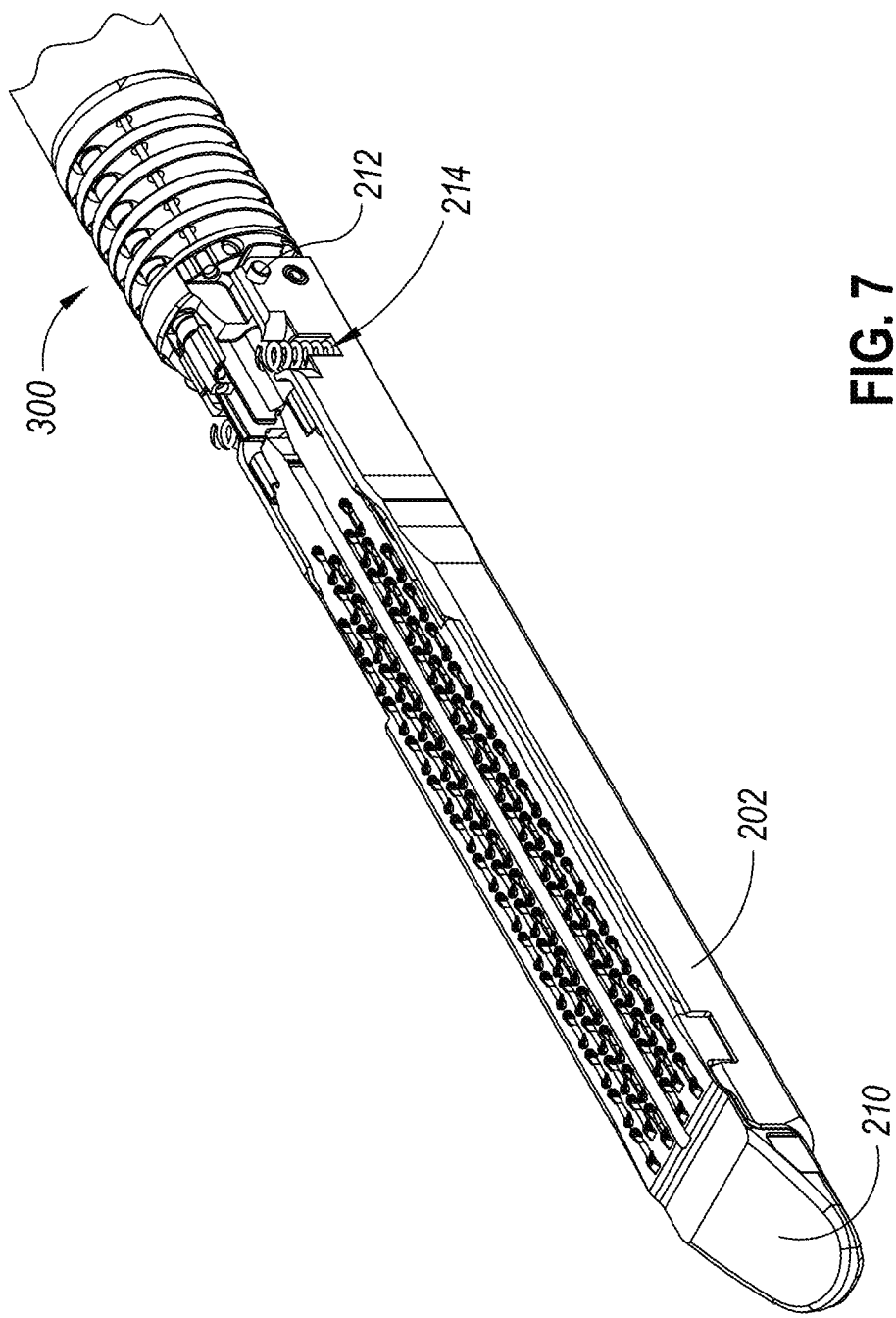
FIG. 7 is an enlarged perspective view of the end effector and the articulation joint of FIG. 3, with an anvil of the end effector omitted.

The anvil jaw 204 has a proximal end 204A, a distal end 204B, and a ramp surface 216 defined at the proximal end 204A, which is described in greater detail below with respect to FIGS. 4 and 9A-9D. The cartridge jaw 202 and anvil jaw 204 are pivotally coupled via a pivot pin 212 that extends through the cartridge jaw 202 and the anvil jaw 204. As seen in FIG. 7, one or more biasing springs 214 extend between the cartridge jaw 202 and anvil jaw 204 to bias the anvil jaw 204 to the open position.

The ramp surface 216 may be visible via a kidney bean-shaped opening 222 (which may be formed as part of the manufacturing process to make the ramp surface 216) that has a first lateral end 222A and a second lateral end 222B. In other words, the kidney bean-shaped opening may be open at its lateral ends 222A, 222B (FIG. 3). As seen in FIG. 4, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately taper, in a distal direction, to a substantially horizontal second angled surface 220.

Figure 8C:
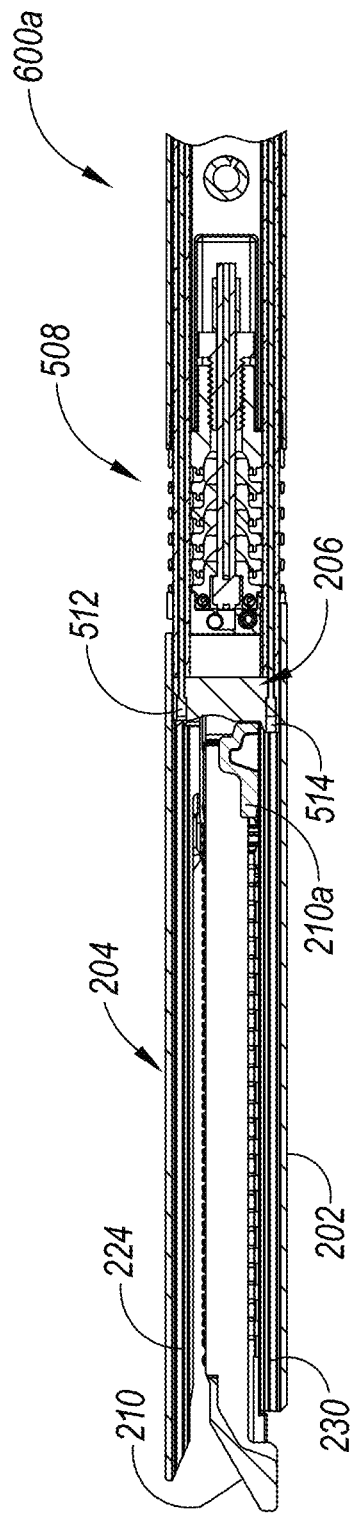
FIG. 8C is a side cross-sectional view of the distal end portion of the surgical instrument of FIG. 1, depicting the anvil in a clamping position with the knife partially advanced.

The anvil jaw 204 further defines a longitudinally extending upper knife channel 224 (see e.g., FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

Figure 17:
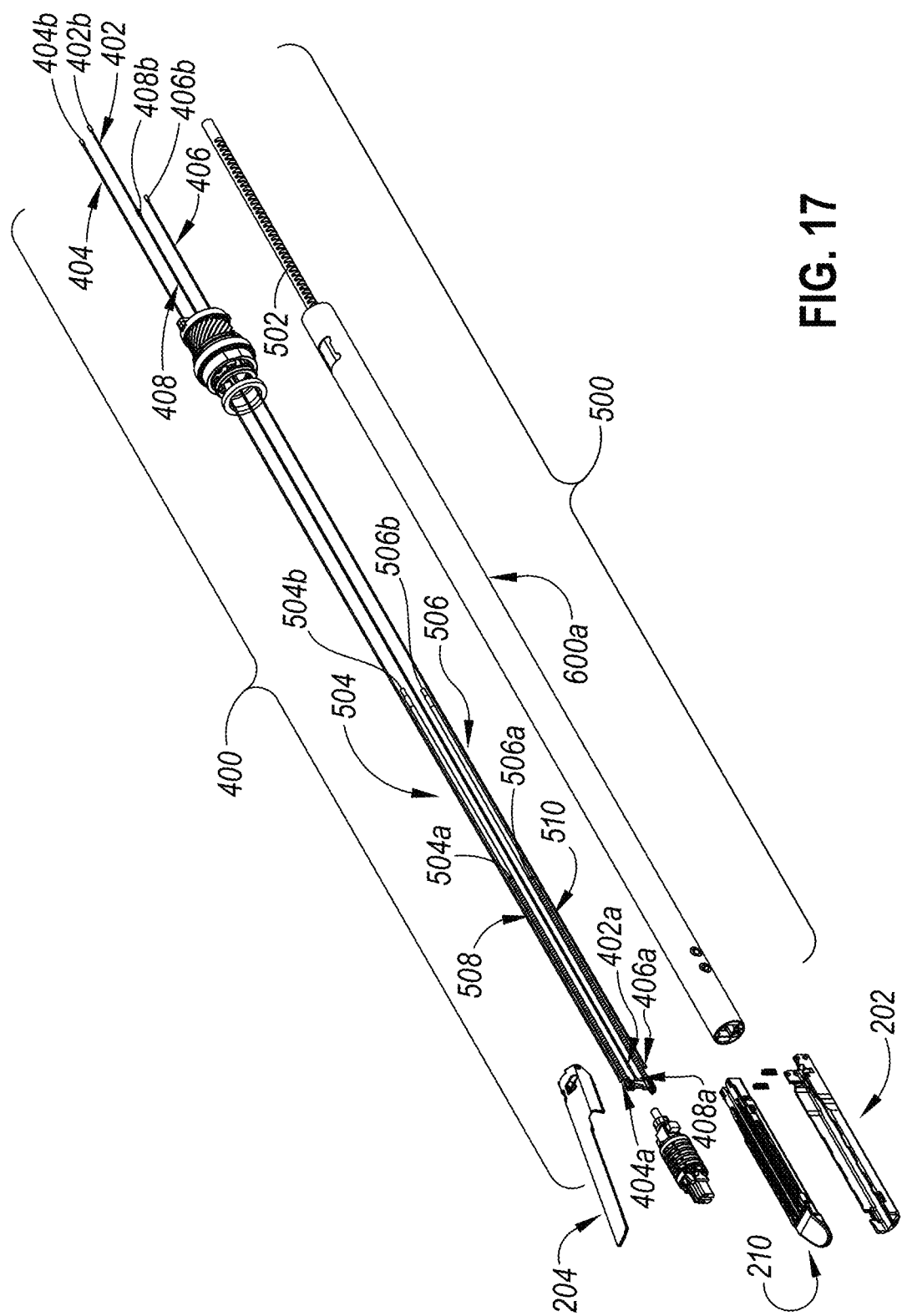
FIG. 17 is an exploded perspective view of a portion of the surgical instrument of FIG. 1, depicting portions of the cable articulation subsystem, the knife firing subsystem, and the roll subsystem.

As shown in FIGS. 2 and 17, the surgical instrument 1000 further comprises a knife firing subsystem 500 operable to close the anvil jaw 204 during a closure stroke. After the end effector 200 is closed, the knife firing subsystem 500 is operable to incise and staple, with staples from the staple cartridge 210, the patient tissue captured between the staple cartridge 210 (which is retained by the cartridge jaw 202) and anvil jaw 204 during a firing stroke.

Figure 6:
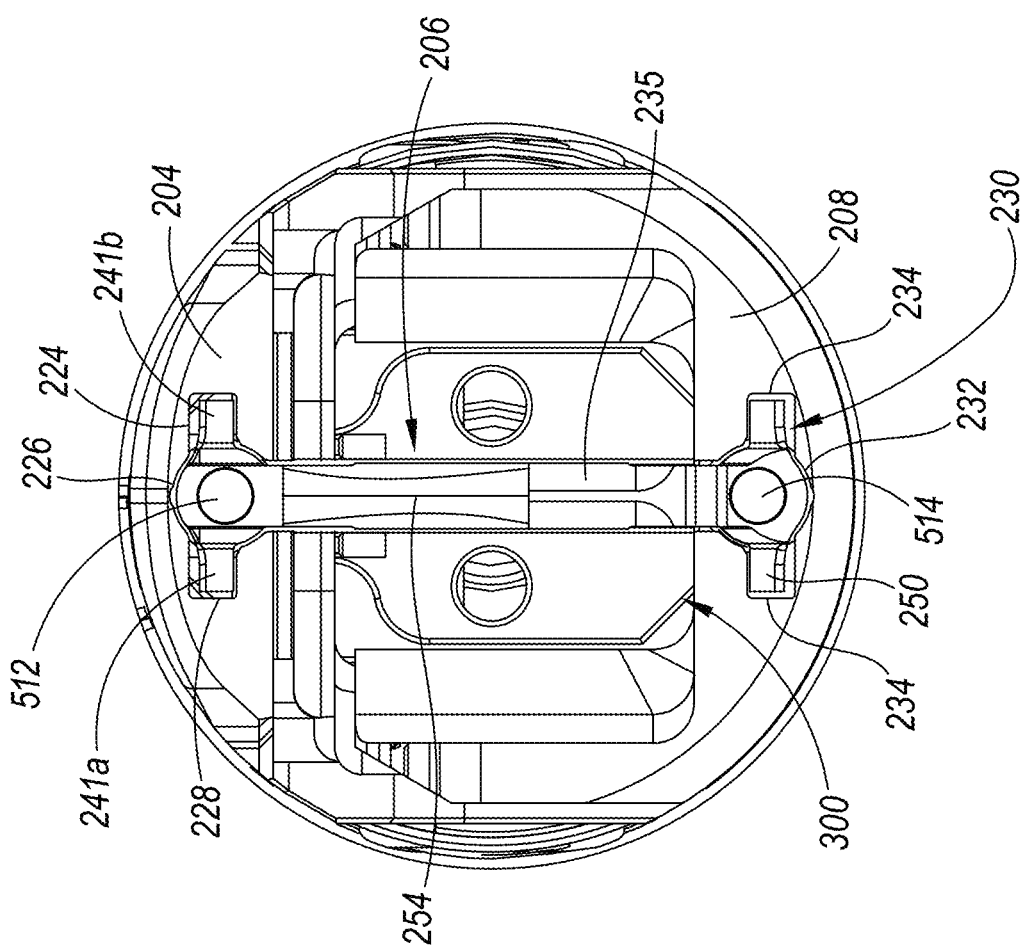
FIG. 6 is an end view of the end effector of FIG. 3.

As shown best in FIGS. 4-6, the knife firing subsystem 500, explained further below in greater detail, includes the knife 206 having a knife sled 236. The knife sled 236 functions as a firing driver by driving cartridge sled 210A distally through a firing stroke, as described below. In some instances, knife sled 236 may be referred to as an I-beam. The knife 206 includes a cutting surface 254. The cutting surface 254 is positioned between the first and second lateral wings 241a, 241b.

The knife sled 236 includes an upper knife tab 238, a lower knife tab 246, and a vertical column 235 coupling and extending between upper knife tab 238 and lower knife tab 246. The upper knife tab 238 includes a centrally disposed cylindrical upper knife tab portion 240 and at least one upper knife tab lateral wing (shown as first and second lateral wings 241a, 241b) that extend away from the upper knife tab portion 240. While the term 'cylindrical' is used, the tab portion need not resemble a perfect cylinder. The knife sled 236 includes at least one lateral wing configured to contact the ramp surface 216. As shown in FIG. 5, the upper knife tab 238 of the knife sled 236 includes first and second lateral wings 241a, 241b configured to contact the ramp surface 216.

The first and second lateral wings 241a, 241b are configured to slidably ride in the upper knife channel 224 to move the anvil jaw 204 between the open position, the grasping position, and the clamping position. Accordingly, the end effector 200 employs "knife-based closure" in which closure of the anvil jaw 204 relative to the cartridge jaw 202 is driven by distal advancement of the knife 206. Each lateral wing 241a, 241b may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some versions, the lower knife tab 246 includes a pair of lateral wings 250. The lower knife tab portion 248 defines a lower knife tab opening 252 that is configured to receive a barrel crimp coupled to a center cable 514, as described in greater detail below.

Figure 8D:
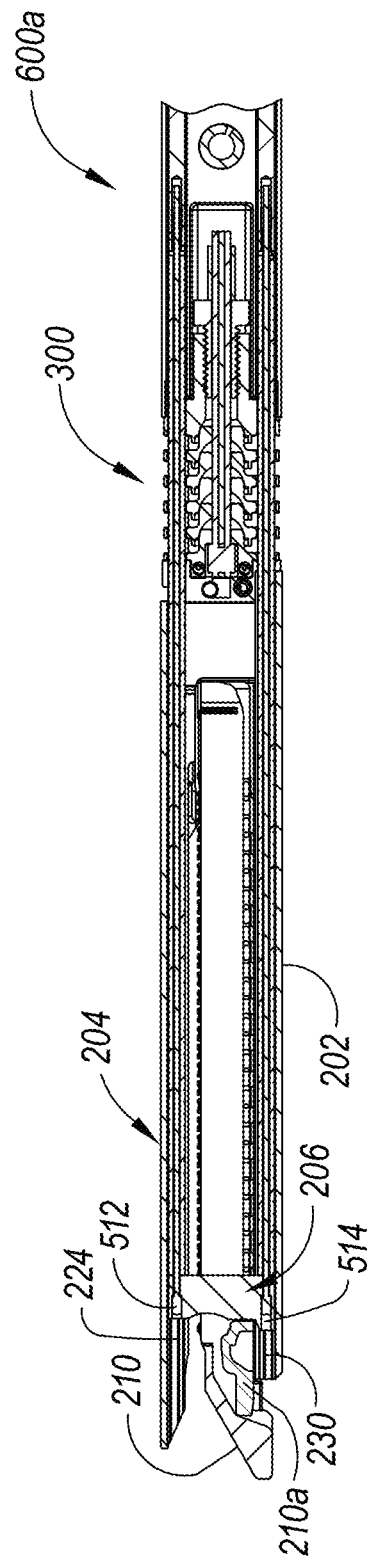
FIG. 8D is a side cross-sectional view of the distal end portion of the surgical instrument of FIG. 1, depicting the anvil in the clamping position with the knife fully advanced.

The staple cartridge 210 may be generally constructed and operable in accordance with the teachings of U.S. patent application Ser. No. 18/588,684, entitled "Methods of Surgical Stapling," filed on Feb. 27, 2024, published as U.S. Pat. Pub. No. 2024/0350137 on Oct. 24, 2024, the disclosure of which is incorporated by reference herein in its entirety. In use, the end effector 200 is positioned relative to patient tissue such that the staple cartridge 210 is disposed on a first side of the tissue and the anvil jaw 204 is positioned on an opposed second side of the tissue. The anvil jaw 204 is then approximated toward the staple cartridge 210 to compress and clamp the tissue against the deck of the staple cartridge 210. Thereafter, the surgical instrument 1000 is fired so that the knife 206 advances distally through the staple cartridge 210 to both cut the clamped tissue using cutting surface 254 and simultaneously actuate staple drivers housed within the staple cartridge 210 to drive an array of staples into the clamped tissue on either side of the cut line. Staple cartridge 210 defines an elongate knife channel 215 dimensioned to receive a portion of vertical column 235 in order to accommodate advancement of the knife 206 through staple cartridge 210. A portion of cartridge sled 210A is slidably housed within elongate knife channel 215 such that the vertical column 235 drives the cartridge sled 210A distally as the knife 206 advances distally in accordance with the description herein (see FIGS. 8C-8D). In some instances, the cartridge sled 210A remains in the distal position (see FIG. 8D) relative to the rest of the staple cartridge 210, even after the knife 206 is retracted proximally after firing the staple cartridge 210 in accordance with the description herein.

As mentioned above, cartridge jaw 202 defines an elongated channel 208 for receiving staple cartridge 210. Additionally, cartridge jaw 202 also defines a lower knife channel 230 (see FIGS. 4, 6, and 8A-9D) dimensioned to slidably receive lower knife tab 246. Referring to FIG. 6, the lower knife channel 230 includes a centrally disposed cylindrical lower knife channel portion 232 and at least one lateral lower knife channel wing 234 that extends away from the lower knife channel portion 232. The cylindrical lower knife channel portion 232 is in communication with elongated channel 208 such that when the staple cartridge 210 is suitably coupled to the cartridge jaw 202, the elongate knife channel 215 of staple cartridge 210 and centrally disposed cylindrical lower knife channel portion 232 are aligned to accommodate actuation of knife sled 236 within both channels 215, 230. The lateral lower knife channel wings 234 are dimensioned to slidably house a respective lower knife tab lateral wing 250. Lower knife tab lateral wings 250 are configured to slidably contact the lateral lower knife channel wings 234 as the knife 206 is advanced in accordance with the description herein. Contact between lower knife tab lateral wings 250 and lateral lower knife channel wings 234 cooperatively assists the lateral wings 241a, 241b and the upper knife channel 224 to close the anvil jaw 204 relative to channel 208 in accordance with the description herein. While the term 'cylindrical' is used, the channel portion 232 need not resemble a perfect cylinder. Other arrangements of staple cavities and staples may be possible. For example, in some versions, a lower knife channel 230 may be defined in the cartridge jaw 202.

The knife 206 is configured to move relative to the first and second jaws 202, 204. The knife 206 is configured to contact the ramp surface 216 to transition the first and second jaws 202, 204 from an open position (see FIG. 8A) to a closed position (see FIG. 8C). As shown in FIGS. 9A-9D, the knife 206 is configured to pivot the second jaw 204 relative to the first jaw 202 as the knife 206 moves distally along the ramp surface 216.

Further to the above, the knife sled 236 is moved distally and proximally by a firing rod 502. The firing rod 502 is configured to apply an indirect force to the knife sled 236, via push coils 508, 510 that directly engage the knife sled 236 (discussed in greater detail below), and push the knife sled 236 toward the distal end of the end effector 200 through a firing stroke. As the firing rod 502 is advanced distally, the knife sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the knife sled 236 distally causes the upper knife tab ramped surface 242A to slide along the anvil ramp surface 216. This movement first urges the anvil jaw 204 closed to a position (e.g., FIGS. 8B and 9B) where a compressive force is applied to the tissue sufficient to grasp it (referred to as the grasping position). Continued movement of the knife sled 236 up the ramp surface 216 (see e.g., FIGS. 8C and 9C) results in a compressive force being applied to the tissue (referred to as the clamping position). As the anvil ramp surface 216 transitions to its substantially horizontally angled surface 220 (see FIGS. 8D and 9D), the upper knife tab 238 can slide within the upper knife channel 224 to drive the stapling and transection of the tissue.

Figure 18:
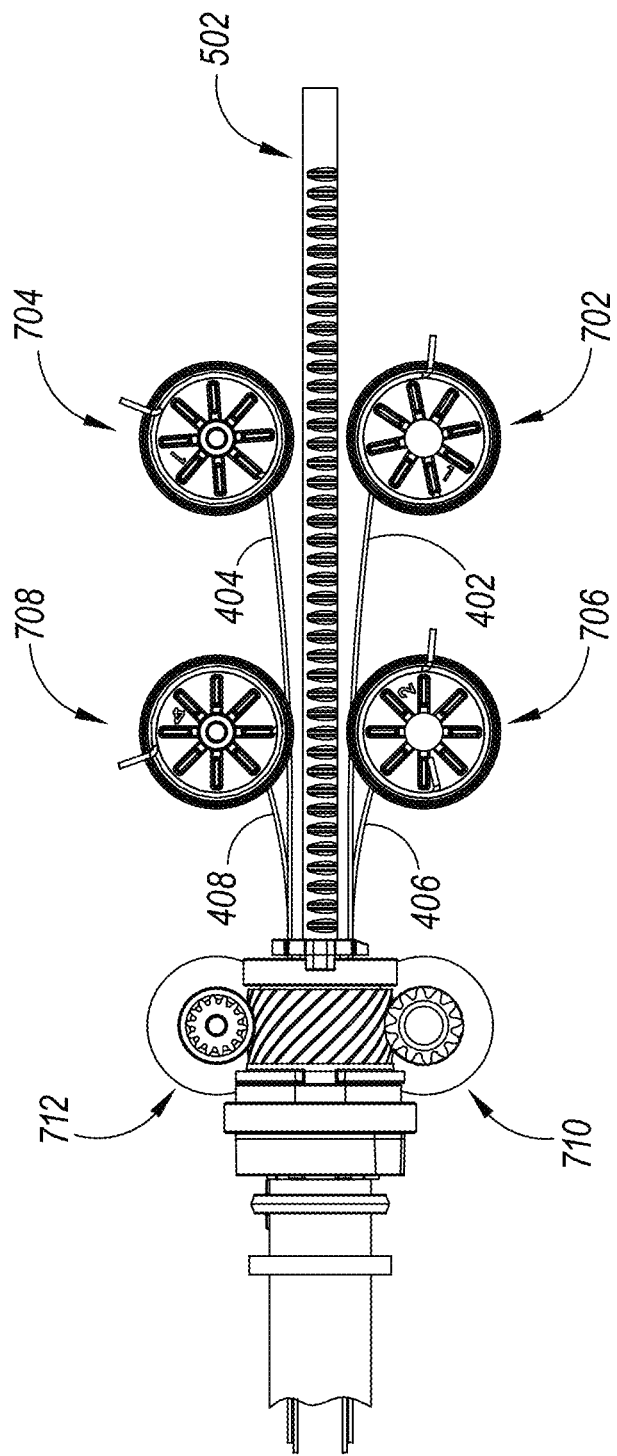
FIG. 18 is a top view of a proximal end of the surgical instrument of FIG. 1, depicting portions of the cable articulation subsystem, the knife firing subsystem, and the roll subsystem.

As shown in FIG. 1, the surgical instrument 1000 further comprises a body exemplified as a housing 700 configured to engage a robotic platform (not shown). In other versions, the body may be configured as a handle (not shown) configured to be gripped and manipulated by a clinician. As best shown in FIGS. 1 and 19, a shaft assembly 600A extends distally from the housing 700 and includes a rotatable outer shaft 602 and an inner shaft 604 arranged in two clamshell halves, with the outer shaft 602 being rotatably mounted to the housing 700 about a rotation joint (not shown), which may include one or more bearings. The inner shaft 604 is rotationally fixed to the outer shaft 602 and is configured such that articulation cables 402, 404, 406, 408 can be partially wound therearound without becoming tangled. As shown in FIG. 18, the housing 700 may house (1) a firing puck assembly 712 (as part of the knife firing subsystem 500 (see FIG. 17)) operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602. In other words, the firing puck assembly 712 connects the motor 1100 to the knife firing subsystem 500, which is used to open/close the end effector, grasp/clamp on tissue, transect tissue, and fire staples.

Referring to FIGS. 10-13, the articulation joint 300 comprises an array of joint discs 302 arranged longitudinally, and a center beam assembly 306 that cooperates with the joint discs 302 to provide articulation of the end effector 200 with at least two degrees of freedom (e.g., yaw and pitch), as described further below. Each joint disc 302 includes a central opening 304 that is configured to align coaxially with the central opening 304 of the other joint discs when the articulation joint 300 is in a straight, non-articulated state. The center beam assembly 306 extends longitudinally through the central openings 304 of joint discs 302 and applies a compressive axial force to the array of joints discs 302 to couple the joint discs 302 with one another. The joint discs 302 are nestably stacked with one another along the center beam assembly 306 such that longitudinally adjacent joint discs 302 movably interface with one another.

Figure 9B:
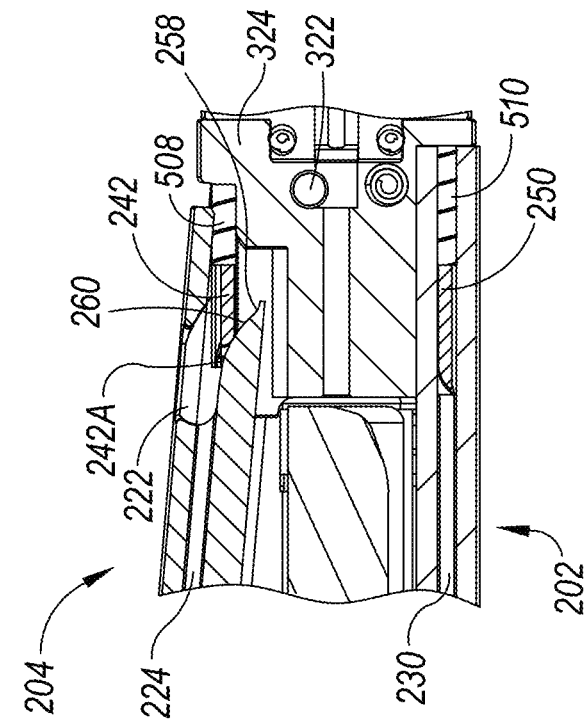
FIG. 9B is an enlarged side cross-sectional view of the proximal end portion of the end effector of the surgical instrument of FIG. 1, depicting the anvil in a grasping position with the knife partially advanced.
Figure 9A:
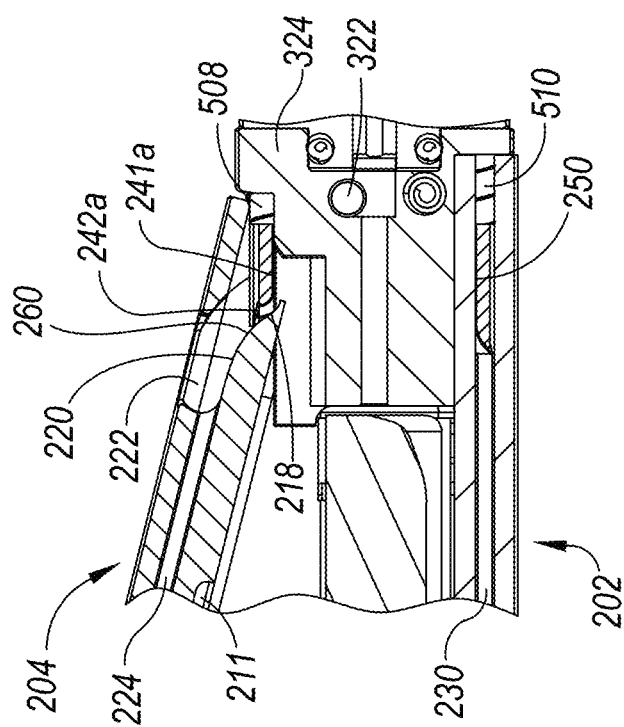
FIG. 9A is an enlarged side cross-sectional view of a proximal end portion of the end effector of the surgical instrument of FIG. 1, depicting the anvil in the open position.
Figure 9C:
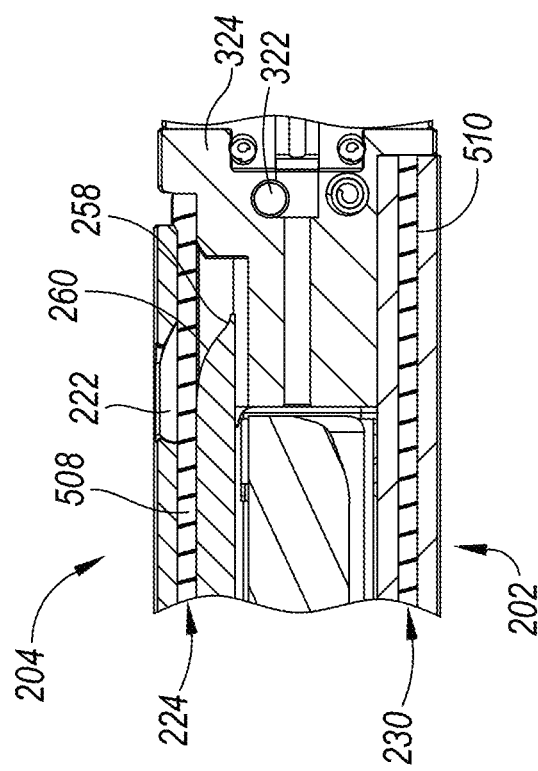
FIG. 9C is an enlarged side cross-sectional view of the proximal end portion of the end effector of the surgical instrument of FIG. 1, depicting the anvil in a clamping position with the knife partially advanced.
Figure 9D:
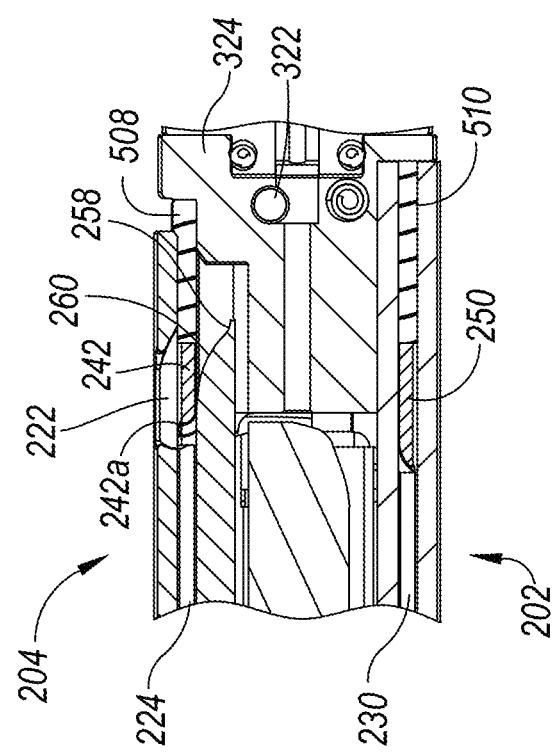
FIG. 9D is an enlarged side cross-sectional view of the proximal end portion of the end effector of the surgical instrument of FIG. 1, depicting the anvil in the clamping position with the knife fully advanced.
Figure 10:
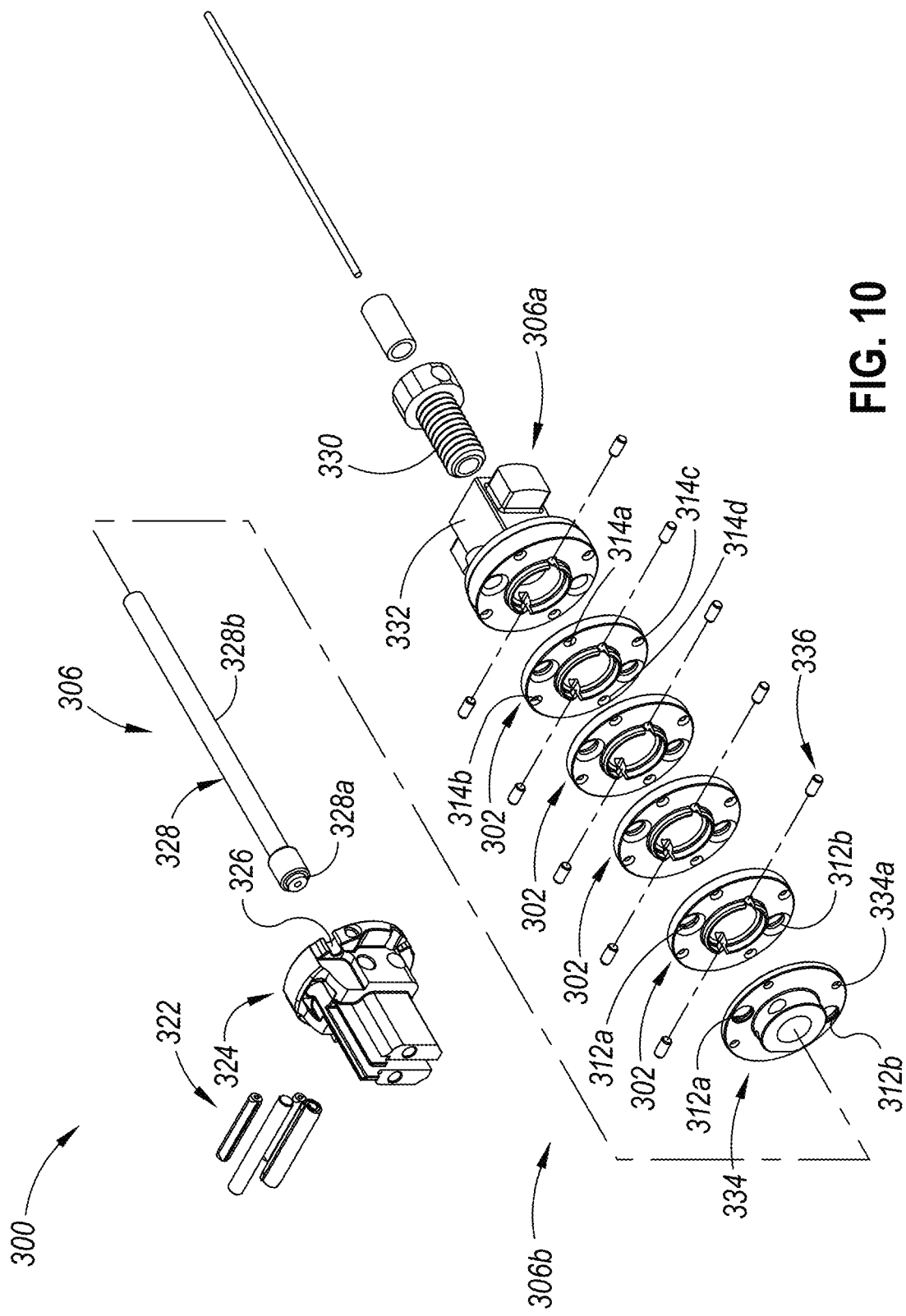
FIG. 10 is an exploded perspective view of the articulation joint of the surgical instrument of FIG. 1.
Figure 11:
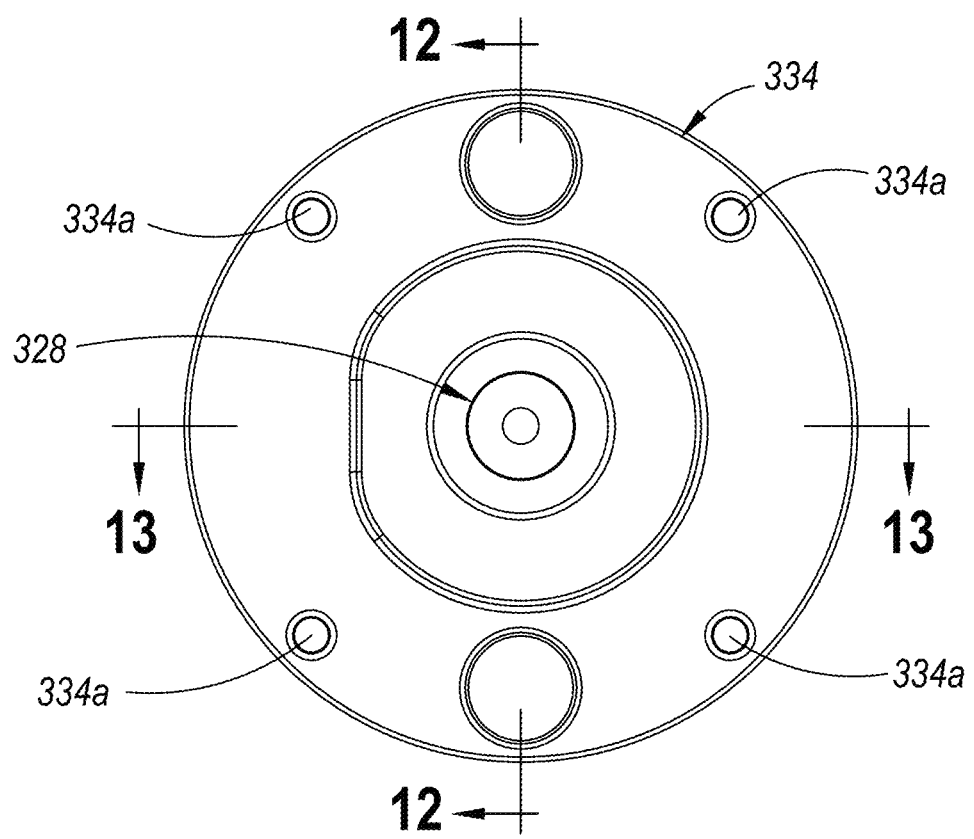
FIG. 11 is an end view of the articulation joint of FIG. 10.

As seen in FIGS. 9A-10, a distal end 306B of the center beam assembly 306 includes a distal retainer 324 that couples the distal end of the articulation joint 300 with a proximal end of the cartridge jaw 202 via one or more fasteners 322, thereby mechanically grounding and retaining the cartridge jaw 202 and thus the end effector 200 relative to the articulation joint 300. The distal retainer 324 includes a plurality of clearance pockets 326 that receive distal ends of articulation cables 402, 404, 406, 408. The distal end 306B further includes a distal retention disc 334 that defines a plurality of cable retention openings 334A. A proximal end 306A of the center beam assembly 306 includes a proximal retainer 332 that couples the proximal end of the articulation joint 300 with a distal end of the shaft assembly 600A.

Figure 12:
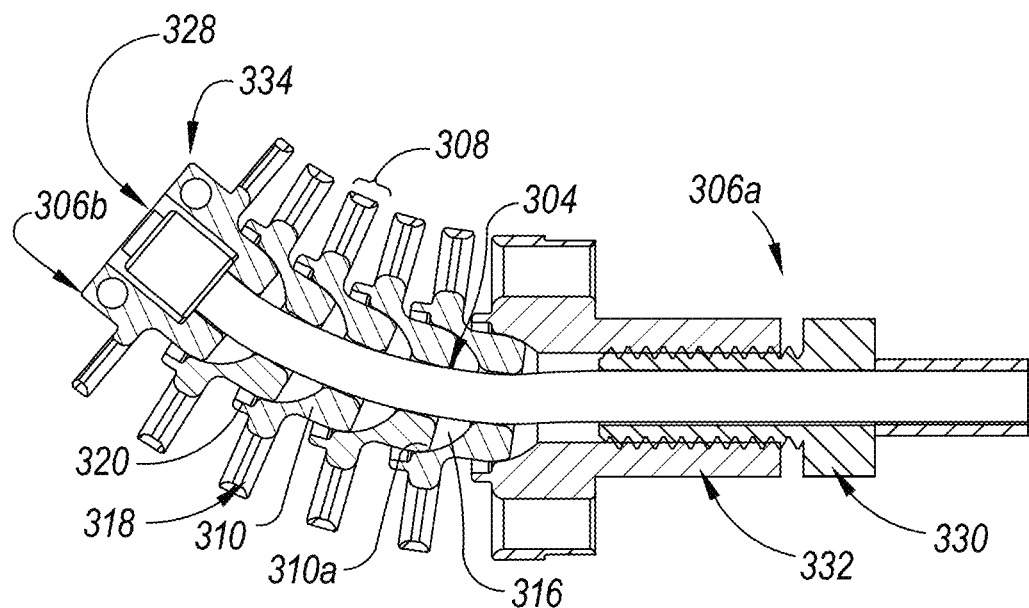
FIG. 12 is a cross-sectional view of a portion of the articulation joint of FIG. 10, taken along line 12-12 in FIG. 11.
Figure 13:
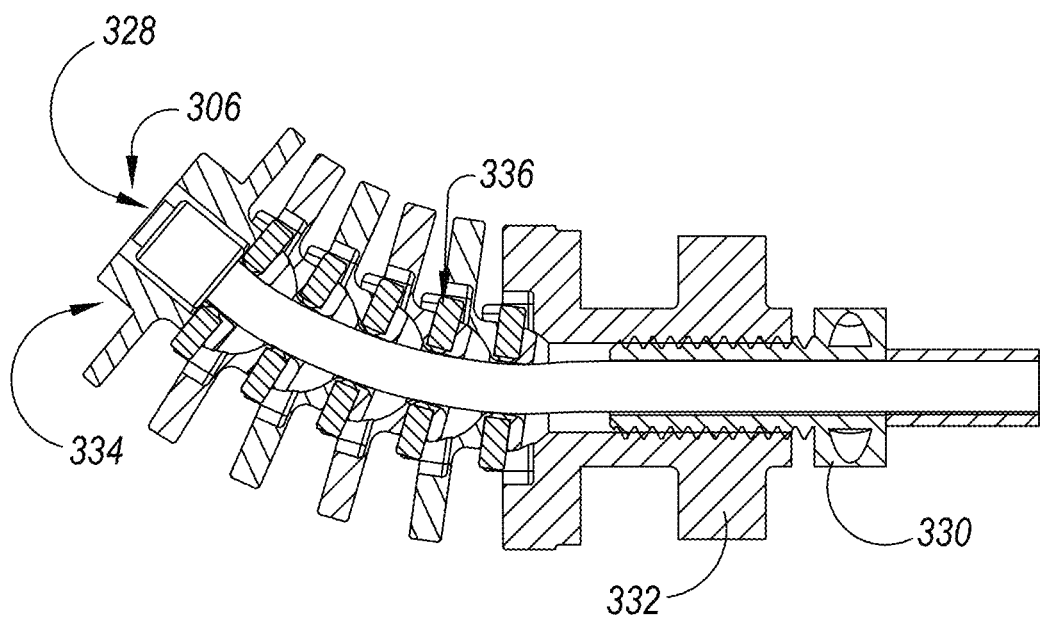
FIG. 13 is a cross-sectional view of a portion of the articulation joint of FIG. 10, taken along line 13-13 in FIG. 11.
Figure 14:
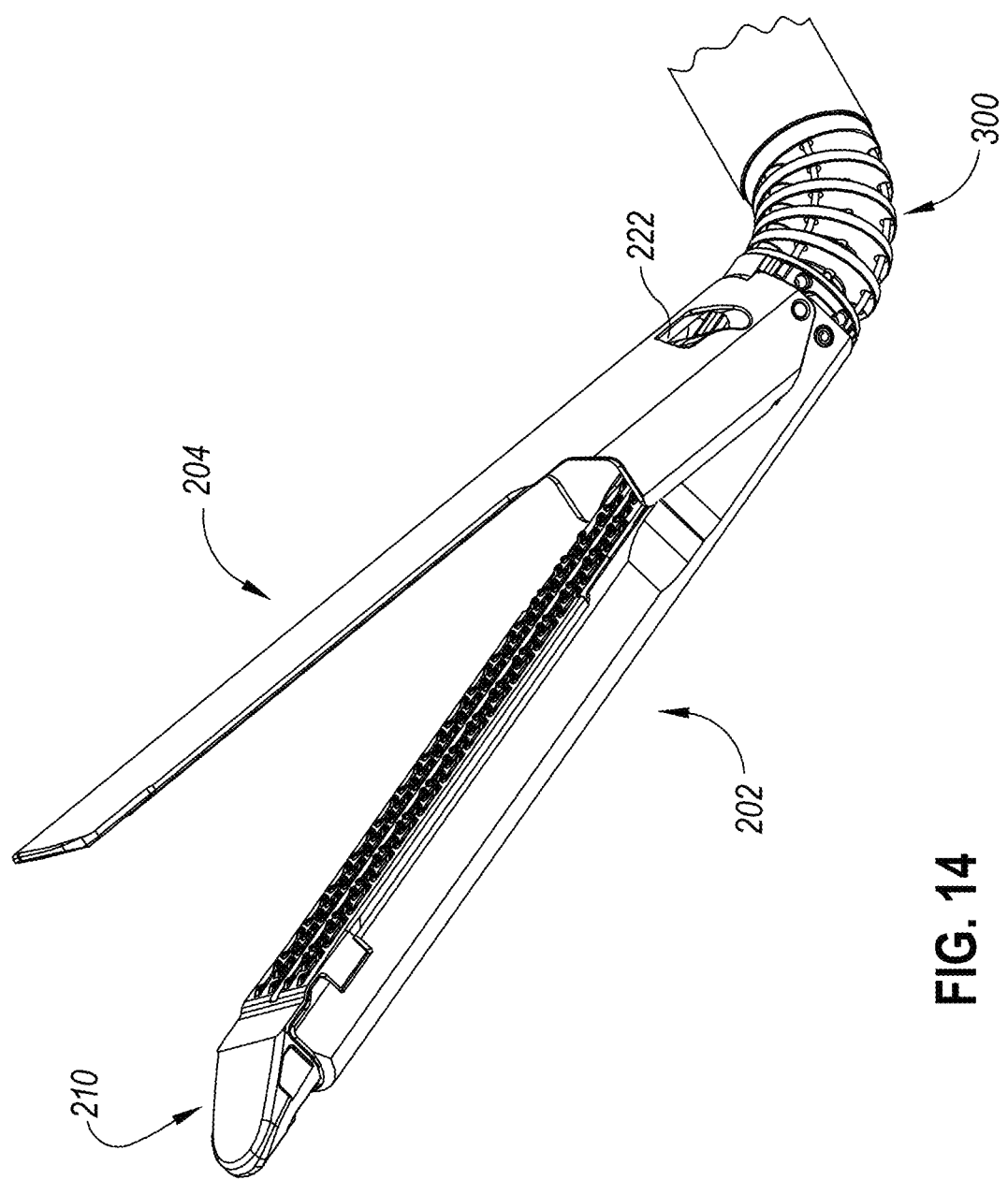
FIG. 14 is a perspective view of the distal end of the surgical instrument of FIG. 1, depicting the end effector articulated vertically and laterally with the anvil open.
Figure 15:
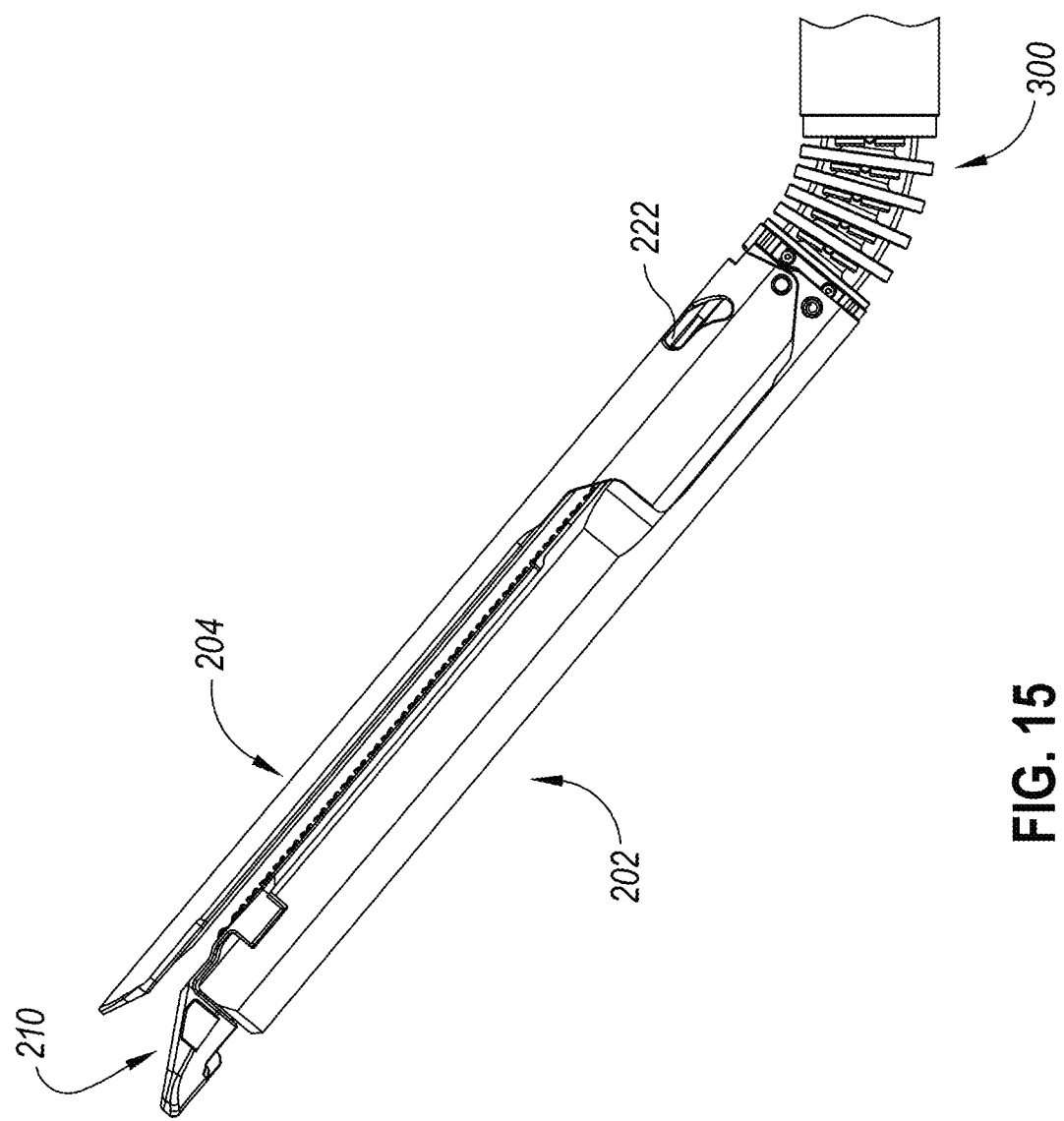
FIG. 15 is a side view of the distal end of the surgical instrument of FIG. 1, depicting the end effector articulated vertically with the anvil closed.
Figure 16:
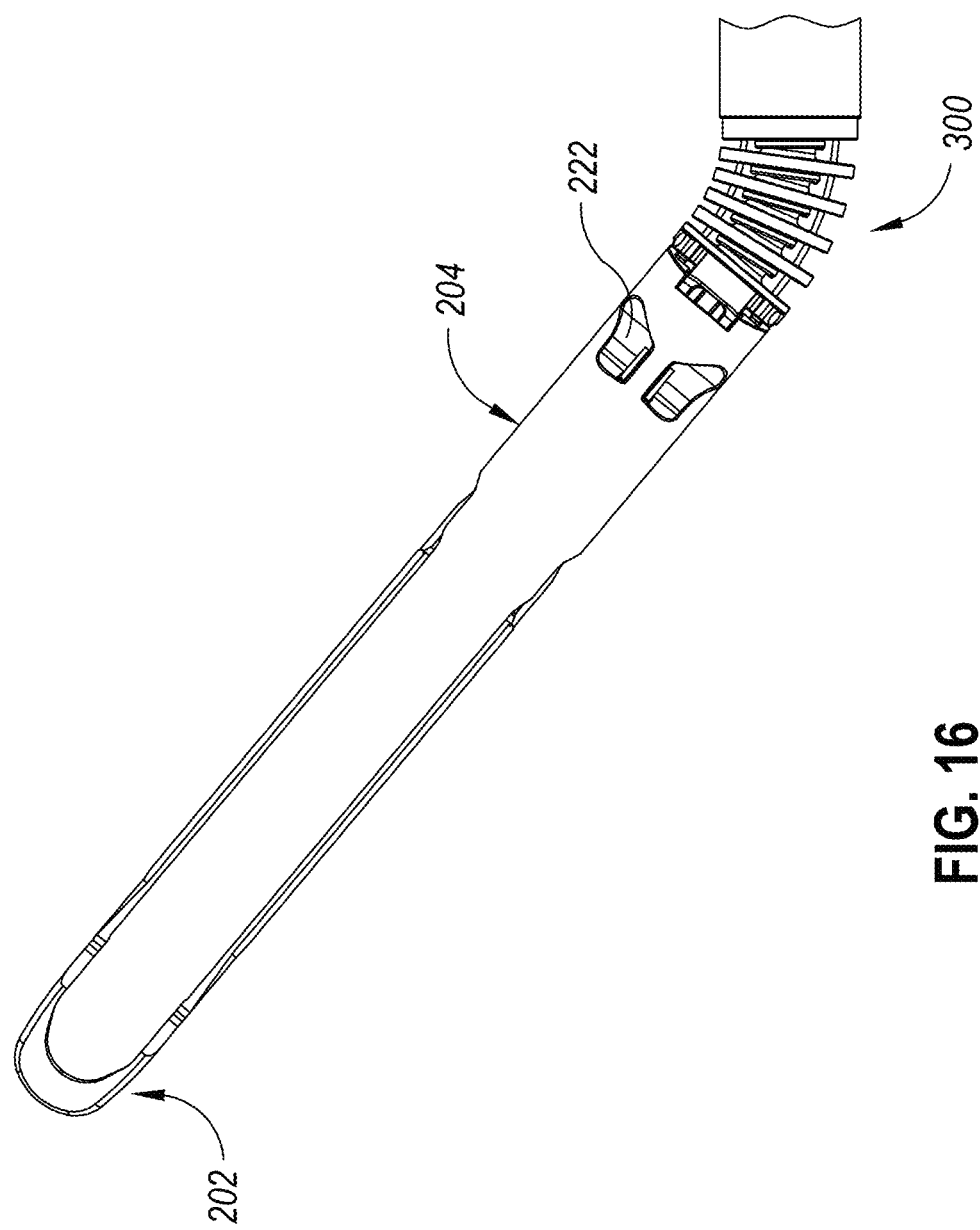
FIG. 16 is a top view of the distal end of the surgical instrument of FIG. 1, depicting the end effector articulated laterally with the anvil closed.

As shown particularly in FIGS. 10, 12, and 13, each joint disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the central opening 304 is defined in the articulation pin 310 of each joint disc 302. In some versions, three articulation cable openings 314A, 314B, 314C are provided to correspond to three articulation cables 402, 404, 406, while in other versions, four articulation cable openings 314A, 314B, 314C, 314D are provided to correspond to four articulation cables 402, 404, 406, 408.

Each joint disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent joint disc 302, with the exception of a 332*d* 310A that engages with the proximal retainer 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one joint disc 302 to the next. In other words, the pins constrain a rotational degree of freedom between adjacent joint discs 302 about the roll axis RA of the surgical instrument 1000. In alternative versions, this feature can be integral to the joint disc 302.

The center beam assembly 306 further includes a center beam 328 that extends longitudinally through the central openings 304 of the joint discs 302. The center beam 328 includes a nitinol core 328A and a stainless-steel collar 328B wound over the nitinol core 328A that allows the center beam 328 to resiliently flex during deflection of the articulation joint 300. The wound stainless-steel collar 328B may have clockwise braiding and counterclockwise braiding to prevent unwinding thereof. The center beam assembly further includes a jack screw 330 that is threadably coupled with the proximal retainer 332 to adjust an axial compression force exerted by the center beam 328 on the array of joint discs 302, thereby enabling adjustment of a pre-load of the articulation joint 300.

The above-described articulation joint 300 forms a portion of the cable articulation subsystem 400 which allows for precise 360-degree movement of the end effector 200 about the articulation joint 300 with at least two degrees of freedom. In some versions, and as dictated by the roll subsystem 600 as well as a need to limit the amount of wrap of the articulation cables 402, 404, 406, 408, the articulation joint 300 is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal retention disc 334 to maintain its positioning. Each articulation cable is discretely manipulable to cause rotation of the articulation joint 300 and end effector 200 about at least one of a pitch axis PA and a yaw axis YA.

In some versions, three articulation cables may be provided rather than the four cables 402, 404, 406, 408 depicted herein. However, four articulation cables 402, 404, 406, 408 circumferentially spaced approximately ninety degrees from one another (as shown) provide load splitting. Additionally, in alternative versions, the articulation cable configuration may be non-symmetric.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. The housing 700 includes articulation puck assemblies 702, 704, 706, 708 with rotatable capstans (not shown) about which corresponding proximal ends 402B, 404B, 406B, 408B of the articulation cables 402, 404, 406, 408 are windably mounted.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the surgical instrument 1000 (through the inner shaft 604).

The articulation cables 402, 404, 406, 408 are routed and coupled to the end effector 200 via the articulation joint 300 such that movement thereof in a proximal direction (via winding about the capstans of the housing 700) causes the end effector 200 to articulate in a predetermined manner via the articulation joint 300. For example, actuation of the first articulation cable 402 in the proximal direction causes articulation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended articulation of the end effector 200. As will be appreciated by those skilled in the art, this configuration provides for the above-mentioned precise 360-degree articulation of the end effector 200 via the articulation joint 300 with at least two degrees of freedom and about 320 degrees of roll.

As shown throughout FIGS. 2, 4, 5, 8A-8D, 9A-9D, 17 and 19, the knife firing subsystem 500 includes the aforementioned knife 206, the aforementioned knife sled 236, a firing rod 502 that drives the knife 206 and/or knife sled 236, a first push rod 504, and a second push rod 506. The firing rod 502 includes a firing rod rack 530 and is driven by a firing puck assembly 712 of the housing 700 which is operatively coupled with the motor 1100. The first push rod 504 has a first push rod distal end 504A coupled to push coil 508 and a first push rod proximal end 504B coupled to the firing rod 502. Similarly, the second push rod has a second push rod distal end 506A coupled to push coil 510 and a second push rod proximal end 506B coupled to the firing rod 502. The distal ends of push coils 508, 510 are coupled to respective upper and lower portions of the knife sled 236 (e.g., the upper knife tab 238 and the lower knife tab 246), which enables the knife 206 to be pushed evenly at its ends. In some versions, the proximal ends 504B, 506B of the push rods 504, 506 are coupled to the firing rod 502 via a differential 520.

The knife firing subsystem 500 is configured in a manner to enable articulation of the end effector 200 while still enabling proper functionality of the knife 206. To that end, the first push rod 504 includes a first flexible section in the form of a first push coil 508 and the second push rod 506 comprises a second flexible section in the form of a second push coil 510. The push coils 508, 510 route through the articulation joint 300 via the respective push coil openings 312A, 312B, and the push rods 504, 506 engage the respective tab openings 244, 252 in the knife sled 236. A first center cable 512 extends through the first push coil 508 to engage the knife sled 236 via a barrel crimp, and a second center cable 514 extends through the second push coil 510 to engage the knife sled 236 via a barrel crimp. The push coils 508, 510 provide the push rods 504, 506 sufficient column strength to deliver an axial firing force to the knife 206, while not being too stiff that would prevent articulation at the joint 300. The cables 512, 514, which are engaged with the knife sled 236 as discussed above (see, e.g., FIG. 8A), prevent the push coils 508, 510 from stretching and/or elongating and serve as retraction cables when the rods 504, 506 are retracted towards the proximal end of the surgical instrument 1000. The entirety of each push rod 504, 506 does not extend through the articulation joint 300, and therefore does not need to be flexible. Accordingly, a proximal section of each push rod 504, 506 can be less flexible than the push coils 508, 510.

II. ILLUSTRATIVE ADAPTIVE KNIFE-BASED CLOSURE METHODS

Knife based clamping for a surgical instrument, such as surgical instrument 1000, uses the same axis to clamp the first and second jaws 202, 204 and to fire the knife 206. In knife-based closures, the knife 206 both closes the first and second jaws 202, 204 and cuts through the tissue. Force control on the clamping region of the anvil jaw (shown as of the second jaw 204) may be desired to modulate clamping speed and/or to reduce the clamping force to achieve the desired clamping (e.g., successfully climb over the ramp surface 216) and firing of the surgical instrument 1000. As a result, it may be beneficial for the controller 1150 to perform an adaptive firing scheme that modulates the speed of clamping, pauses, and/or adjusts the maximum force threshold to achieve the desired clamping on thick tissue.

Figure 20A:
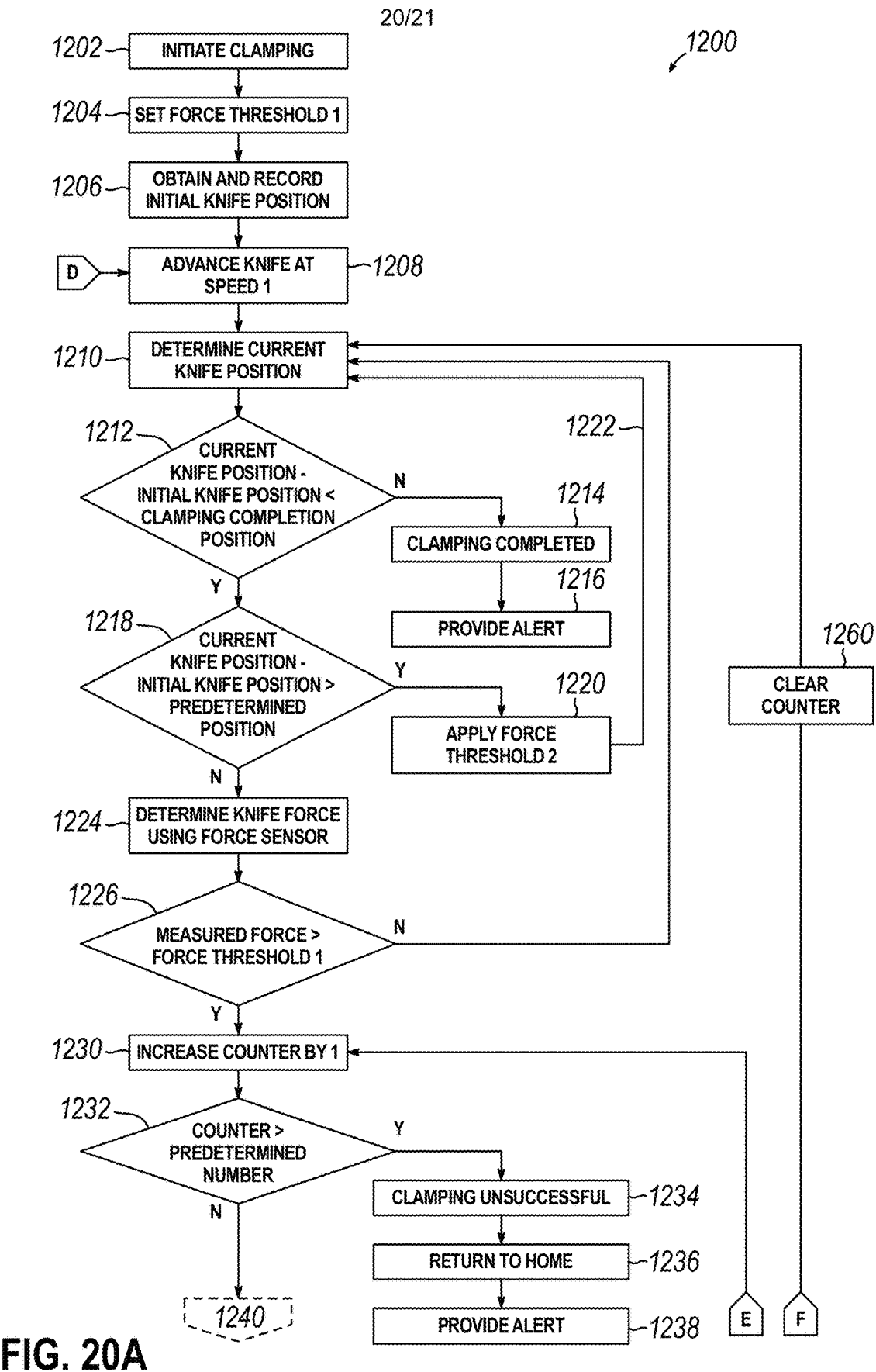
FIG. 20A is a first portion of a diagrammatic view depicting an illustrative method for controlling the surgical instrument of FIG. 1.
Figure 20B:
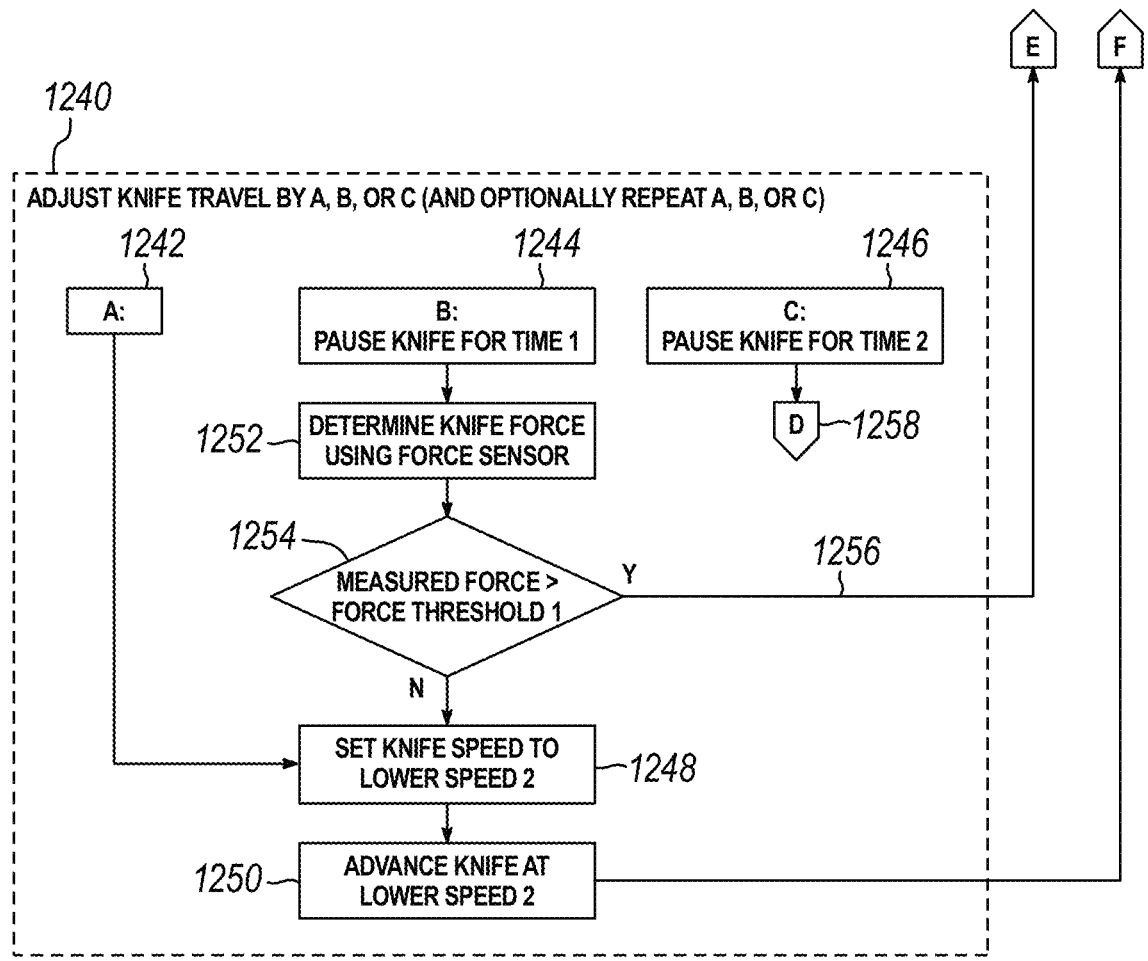
FIG. 20B is a second portion of a diagrammatic view that together with the first portion of FIG. 20A depict an illustrative method for controlling the surgical instrument of FIG. 1.

A method 1200 of operating the surgical instrument 1000 is illustrated and described with reference to FIGS. 20A-20B. At step 1202, the user or the controller 1150 initiates the clamping sequence, which may be automatically or manually initiated. The method 1200 uses force feedback from the motor 1100 in the housing 700 to modulate speed and duration of clamping with knife-based closure of the surgical instrument 1000. The method 1200 reduces force peaks (force spikes) by smoothing out force peaks in real time.

At step 1204, the controller 1150 is configured to set/define a first force threshold. This first force threshold may be based on the torque capacity of the motor 1100, past usage data from the same or similar surgical instruments 1100, and/or data available to either the controller 1150 from the memory 1152 or received by the controller 1150 from a cloud, and/or other information. For example, this force threshold may be based on a percentage of torque available to the motor during clamping (e.g., about 80% of the available torque of the motor 1100). Clamping too much tissue may result in the knife 206 being unable to advance. Having a threshold that is less than the maximum available torque prevents damage to the motor 1100 during operation of the surgical instrument 1000.

At step 1206, the position sensor 1102 obtains and communicates with the controller 1150 to record an initial position of knife 206. In some versions, this step may be omitted. In some versions, the position sensor 1102 may include a linear, rotary, angular, absolute, gradual, contact, and non-contact sensor configured to sense the knife firing subsystem 500. In some versions, the position sensor 1102 includes a linear encoder configured to sense a predetermined region of the knife firing subsystem 500.

At step 1208, the method 1200 includes advancing the knife 206 along the ramp surface 216 at a first speed (speed 1). This advancement of the knife 206 transitions the first and second jaws 202, 204 from an open position to a closed position, with the degree of closure based on the degree of advancement of the knife 206 using the knife firing subsystem 500.

At step 1210, the current position of the knife 206 is determined. The position of the knife 206 may be obtained using a variety of methods such as through the use of the position sensor 1102 as described above in step 1206. In some versions, the position of the motor 1100 may be determined without the use of the position sensor 1102.

At step 1212, the controller 1150 is configured to determine whether the knife 206 has reached a first predetermined position on the ramp surface 216. For example, step 1212 may determine whether the difference between the current knife position determined at step 1210 and the initial knife position determined at step 1206 is less than the clamping completion position. In other words, the controller 1150 determines whether the current knife position determined at step 1210 minus the initial knife position determined at step 1206 is less than the clamping completion position. The clamping completion position indicates the first and second jaws 202, 204 are in the closed position and no additional clamping is desired. The clamping completion position may be a value stored on the memory 1152 of the controller 1150. In some versions, the clamping completion position may be about 8 millimeters; however, this clamping completion position may vary depending on the surgical instrument 1000 and/or the staple cartridge 210. In some versions, the initial knife position may simply be zero.

At step 1214, in response to the difference between the current position of the knife 206 determined at step 1210 and the initial knife position determined at step 1206 being equal to or greater than the clamping completion position, the clamping is completed. Optionally, at step 1216, an alert may be provided to the user. This alert may be one or more of a visual, audio, or tactile alert provided to the user. In some versions, this clamping completion position represents when the ramp surface 216 is completely overcome (e.g., in some surgical instruments 1000 may be about 8 millimeters).

At step 1218, in response to the difference between the current knife position determined at step 1210 and the initial knife position determined at step 1206 being less than the clamping completion position, this difference is then compared against a predetermined distance. The predetermined distance may be a value stored on the memory 1152 of the controller 1150. In some versions, the predetermined distance may be about 2 to about 4 millimeters; however, this predetermined distance may vary depending on the surgical instrument 1000 and/or the staple cartridge 210. The knife firing subsystem 500 can handle more axial load the further the knife 206 travels into the end effector 200. As a result, the knife 206 reaching this predetermined distance indicates the knife 206 has sufficiently advanced to a point where the force threshold can be increased. Steps 1212 and 1218 collectively create three "zones" or "regions."

At step 1220, in response to determining the knife 206 has reached the first predetermined position on the ramp surface 216, the controller 1150 is configured to apply a second predetermined force threshold that is greater than the first predetermined force threshold. This second predetermined force threshold may be a value stored on the memory 1152 of the controller 1150. While only one additional force threshold (the second predetermined force threshold) is shown in FIG. 20A, additional force thresholds are also envisioned. These additional force thresholds allow the controller 1150 to increase the predetermined force threshold as the knife 206 moves distally along the ramp surface 216. As shown by arrow 1222, after step 1220, the method proceeds to step 1210 of determining the current knife position.

At step 1224, in response to determining the knife 206 has not reached the first predetermined position on the ramp surface 216, the method 1200 includes determining the first measured knife force value using the force sensor 1104. Step 1224 includes obtaining, using the force sensor 1104, the first force value exerted by the motor 1100 as the knife 206 is contacting the ramp surface 216. Step 1224 also includes communicating from the force sensor 1104 to the controller 1150 the first force value exerted by the motor 1100 as the knife 206 is contacting the ramp surface 216.

At step 1226, the method 1200 includes the controller 1150 determining whether the measured first force value exerted by the motor 1100 exceeds the first predetermined force threshold as the knife 206 is contacting the ramp surface 216.

As shown by arrow 1228, in response to determining the first force value exerted by the motor 1100 does not exceed the first predetermined force threshold as the knife 206 is contacting the ramp surface 216, the method 1200 includes permitting the knife to continue on and not altering the travel of the knife 206. As shown by arrow 1228, if the first measured force value exerted by the motor 1100 does not exceed the first predetermined force threshold as the knife 206 is contacting the ramp surface 216, a new current position of the knife 206 is determined using the position sensor 1102 at step 1210. As a result, the method 1200 proceeds again from step 1210. This new current knife position replaces the prior knife position previously described above with reference to steps 1212 and 1218. This loop continues on until (1) the clamping completion position is reached in step 1212, or (2) the measured force value exerted by the motor 1100 exceeds the first predetermined force threshold of step 1226. If the predetermined position is reached in step 1218, the loop continues on albeit on a high force threshold as described in step 1220.

At step 1230, if the first measured force value exerted by the motor 1100 exceeds the first predetermined force threshold as the knife 206 is contacting the ramp surface 216, the controller 1150 increases the counter by one unit.

At step 1232, the controller 1150 determines whether the counter exceeds a predetermined number of attempts. The predetermined number of attempts may be fixed or may change based on feedback received by the controller 1150. In some versions, the predetermined number of attempts is about 50 attempts. In some versions, if the first measured force value significantly exceeds the first predetermined force threshold, the predetermined number of attempts may be reduced. Alternatively, if the first measured force value is close to the first predetermined force threshold, the predetermined number of attempts may be increased. This counting allows for termination of the method to prevent a continuous loop.

At step 1234, if the counter exceeds the predetermined number of attempts, the clamping is considered unsuccessful. This unsuccessful clamping indicates that the first force value exerted by the motor 1100 is not reduced quick enough. At step 1236, the controller 1150 is configured to actuate the knife firing subsystem 500 to return the knife 206 to the home position without the knife 206 transitioning the first and second jaws 202, 204 to the closed position. In other words, if after a predetermined number attempts the knife 206 is unable to climb over the ramp surface 216, the knife 206 may abort the clamping and return to the home position. Optionally, at step 1238, an alert may be provided to the user indicating the unsuccessful clamping. This alert may be one or more of a visual, audio, or tactile alert.

At step 1240, the method 1200 includes altering travel of the knife 206 in response to the determination at step 1228. At step 1240, the controller 1150 is configured to alter travel of the knife 206 by performing at least one of steps 1242, 1244, 1246. In other words, the travel of the knife 206 may be altered using any one or more of steps 1242, 1244, 1246. One or more of steps 1242, 1244, 1246 are desirable when trying to clamp over thick tissue, to lower the clamping force by either modulating the clamping speed or even stopping and waiting for the tissue to flow and relax. When tissue relaxation occurs, the clamping force is reduced, allowing a reduced torque output from the motor 1100. This may also protect the knife firing subsystem 500 from mechanical stress that may inadvertently damage the surgical instrument 1000. It may be desirable to smooth out clamping force spikes in the knife firing subsystem 500 in real time due to tissue encountered.

At step 1248, the controller 1150 may set or define a second speed (speed 2) that is less than the first speed. The difference between the first and second speeds may vary. In some versions, the second speed may be about half of the first speed. For example, the first speed may be about 1.5 millimeters/second, and the second speed may be about 0.75 millimeters/second. At step 1250, the controller 1150 advances the knife 206 at the second speed. Unlike steps 1244 and 1246, step 1242 does not stop the knife 206, but instead, reduces the speed of the knife 206. In some versions, the options provided by steps 1242 and 1246 may be removed, resulting in step 1244 being the only option of carrying out step 1240 of altering the travel of knife 206.

At step 1244, the controller 1150 may pause the knife 206 for a predetermined time. In some versions, the predetermined time may be about 2 seconds; however, this predetermined time may vary the measured force, the surgical instrument 1000, and/or the staple cartridge 210. For example, the predetermined time may vary depending on the measured knife force determined in step 1224, or the magnitude of difference between the measured knife force and the first force threshold of step 1226.

At step 1252, similar to step 1224, the method 1200 includes obtaining, using the force sensor 1104, the measured force value of step 1252 exerted by the motor 1100 as the knife 206 is contacting the ramp surface 216. In other words, at step 1252, the force sensor 1104 is configured to obtain a second force value exerted by the motor 1100 as the knife 206 is contacting the ramp surface 216. Step 1252, similar to step 1224, includes communicating from the force sensor 1104 to the controller 1150 the measured force value of step 1252 exerted by the motor 1100 as the knife 206 is contacting the ramp surface 216. The method 1200 checks for force on the knife 206 after the predetermined amount of time (e.g., about 2 seconds) elapse.

At step 1254, similar to step 1226, the controller 1150 is configured to determine whether the measured force value of step 1252 exerted by the motor 1100 exceeds the first predetermined force threshold as the knife 206 is contacting the ramp surface 216. If the measured force value of step 1252 exceeds the first predetermined force threshold, as shown by arrow 1256, the counter of the controller 1150 is increased by one unit as described above with reference to step 1230. This process is repeated until either the measured force value exerted by the motor 1100 no longer exceeds the first predetermined force threshold or the counter exceeds the predetermined number of attempts of step 1232. In other words, if the force drops below the predetermined threshold, the knife 206 advances at a reduced speed, lower than the speed of step 1208, until the knife 206 encounters again where the measured force exceeds the first force threshold (see steps 1226 and 1254). The measured force at step 1252 may be less than the measured force at step 1224 given the pause of the knife 206 at step 1244 given the viscoelastic effect of tissue. The knife 206 may pause again (see steps 1244 or 1246) until the force on the knife 206 drops. If on the other hand, the knife 206 is able to progress over the ramp surface 216 in small steps separated by pauses, the force threshold may be increased the more the knife travels further over the ramp (see step 1220).

At step 1246, the controller 1150 may pause the knife 206 for a second predetermined amount of time. The first predetermined amount of time of step 1244 may be the same or different than the second predetermined amount of time of step 1246. In response to pausing the knife 206 for the second predetermined amount of time. For steps 1244 and 1246, if during clamping at a pre-determined speed, the motor 1100 exceeds a certain force threshold, the knife 206 pauses over the ramp surface 216 for a predetermined time.

In response to advancing the knife 206 at the second speed at step 1250, at step 1260, the counter of the controller 1150 may optionally be reset to zero, prior to proceeding back to step 1210 of determining the new position of the knife 206.

In response to altering travel of the knife 206 at step 1240, the method 1200 may repeat any one or more of steps 1242, 1244, 1246. For example, on a second or subsequent (e.g., third, fourth, or so on) the same or different 1242, 1244, 1246 may be utilized. For example, on a second or subsequent (e.g., third, fourth, or so on) iteration of step 1244, the method 1200 includes pausing the knife 206 until a measured force value (e.g., a third force value, a fourth force value, or an additional force value) exerted by the motor 1100 is below the second predetermined force threshold while the knife 206 is contacting the ramp surface 216. For example, on a second or subsequent (e.g., third, fourth, or so on) iteration of step 1248, the method 1200 includes advancing the knife 206 at a third speed that is less than the second speed. In some versions, the duration of this subsequent pause may be more or less than the duration of the first initial pause of step 1244.

III. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus (1000) comprising: (a) an end effector (200) operable to clamp, staple, and cut tissue, comprising: (i) a first jaw (202) configured to selectively receive a staple cartridge (210), (ii) a second jaw (204), wherein at least one of the first or second jaws includes a ramp surface (216), and (iii) a knife (206) configured to move relative to the first and second jaws, wherein the knife is configured to contact the ramp surface to transition the first and second jaws from an open position to a closed position; (b) a motor (1100) configured to actuate the knife along a firing stroke while the staple cartridge is housed within the first jaw to thereby cut tissue clamped by the first and second jaws; (c) a sensor (1104) configured to sense force exerted by the motor; and (d) a controller (1150) in communication with the motor and the sensor, the controller configured to: (i) advance the knife along the ramp surface at a first speed, (ii) obtain using the sensor a first force value exerted by the motor as the knife is contacting the ramp surface, (iii) determine whether the first force value exerted by the motor exceeds a first predetermined force threshold as the knife is contacting the ramp surface, and (iv) in response to determining the first force value exerted by the motor exceeds the first predetermined force threshold as the knife is contacting the ramp surface, altering travel of the knife by at least one of the following: (A) pause the knife for a predetermined amount of time, (B) pause the knife until a second force value exerted by the motor obtained from the sensor is below the first predetermined force threshold, or (C) advance the knife at a second speed that is less than the first speed.

Example 2

The apparatus (1000) of Example 1, wherein the controller is configured to alter the travel of the knife by both: (A) pausing the knife for a predetermined amount of time, and (B) after pausing the knife for a predetermined amount of time, advancing the knife at a second speed that is less than the first speed.

Example 3

The apparatus (1000) of any one or more of Examples 1 through 2, wherein after pausing the knife for the predetermined amount of time and prior to advancing the knife at the second speed, the controller is configured to: (i) communicate from the sensor a second force value exerted by the motor as the knife is contacting the ramp surface, and (ii) determine whether the first force value exerted by the motor exceeds the first predetermined force threshold as the knife is contacting the ramp surface.

Example 4

The apparatus (1000) of any one or more of Examples 1 through 3, wherein after advancing the knife at the second speed, the controller is configured to: (i) obtain from the sensor a third force value exerted by the motor caused by tissue resistance on the knife while the knife is contacting the ramp surface, (ii) determine whether the third force value of the motor exceeds the first predetermined force threshold, and (iii) in response to determining the third force value of the motor exceeds the first predetermined force threshold, alter travel of the knife.

Example 5

The apparatus (1000) of Example 4, wherein altering the travel of the knife in response to determining the third force value of the motor exceeds the first predetermined force threshold further comprises at least one of the following: (A) pause the knife for a second predetermined amount of time, (B) pause the knife until a third force value exerted by the motor is below the first predetermined force threshold, or (C) advance the knife at a third speed, that is equal to or less than the second speed.

Example 6

The apparatus (1000) of any one or more of Examples 1 through 5, wherein the controller is configured to, in response to the first force value exerted by the motor not reducing to below the first predetermined force threshold after a predetermined number of attempts, return the knife to a home position without the knife transitioning the first and second jaws to the closed position.

Example 7

The apparatus (1000) of any one or more of Examples 1 through 6, wherein the sensor comprises a torque sensor configured to sense torque of the motor.

Example 8

The apparatus (1000) of any one or more of Examples 1 through 7, further comprising a shaft assembly (600A) extending proximally from the end effector along a shaft axis (SA), wherein the motor is coaxially positioned along the shaft axis.

Example 9

The apparatus (1000) of Example 8, further comprising a housing extending proximally from the shaft assembly, wherein the motor and the sensor are positioned within the housing.

Example 10

The apparatus (1000) of any one or more of Examples 1 through 9, wherein the controller is configured to increase the first predetermined force threshold as the knife moves distally along the ramp surface.

Example 11

The apparatus (1000) of any one or more of Examples 1 through 10, wherein the knife is configured to pivot the second jaw relative to the first jaw as the knife moves distally along the ramp surface.

Example 12

The apparatus (1000) of any one or more of Examples 1 through 11, wherein the second jaw includes a plurality of staple forming pockets (211), wherein the ramp surface is integrally formed together as a unitary piece together with the second jaw.

Example 13

The apparatus (1000) of any one or more of Examples 1 through 12, wherein the ramp surface includes a concave portion (258) and a convex portion (260), wherein the concave portion is proximal to the convex portion.

Example 14

The apparatus (1000) of any one or more of Examples 1 through 13, wherein the knife includes a knife sled (236), wherein the knife sled includes at least one lateral wing (241a, 241b) configured to contact the ramp surface.

Example 15

The apparatus (1000) of any one or more of Examples 1 through 13, wherein the knife includes a cutting surface (254), wherein the knife sled includes first and second lateral wings (241a, 241b) configured to contact the ramp surface, wherein the cutting surface is positioned between the first and second lateral wings.

The following clauses also relate to various non-exhaustive ways in which the teachings herein may be combined or applied.

Clause 1. An apparatus comprising:
(a) an end effector operable to clamp, staple, and cut tissue, comprising:
   (i) a first jaw configured to selectively receive a staple cartridge,
   (ii) a second jaw, wherein at least one of the first or second jaws includes a ramp surface, and
   (iii) a knife configured to move relative to the first and second jaws, wherein the knife is configured to contact the ramp surface to transition the first and second jaws from an open position to a closed position;
(b) a motor configured to actuate the knife along a firing stroke while the staple cartridge is housed within the first jaw to thereby cut tissue clamped by the first and second jaws;
(c) a sensor configured to sense force exerted by the motor; and
(d) a controller in communication with the motor and the sensor, the controller configured to:
   (i) advance the knife along the ramp surface at a first speed,
   (ii) obtain using the sensor a first force value exerted by the motor as the knife is contacting the ramp surface,
   (iii) determine whether the first force value exerted by the motor exceeds a first predetermined force threshold as the knife is contacting the ramp surface, and
   (iv) in response to determining the first force value exerted by the motor exceeds the first predetermined force threshold as the knife is contacting the ramp surface, altering travel of the knife by at least one of the following:
      (A) pause the knife for a predetermined amount of time,
      (B) pause the knife until a second force value exerted by the motor obtained from the sensor is below the first predetermined force threshold, or (C) advance the knife at a second speed that is less than the first speed.

Clause 2. The apparatus of clause 1, wherein the controller is configured to alter the travel of the knife by both:
(A) pausing the knife for a predetermined amount of time, and
(B) after pausing the knife for a predetermined amount of time, advancing the knife at a second speed that is less than the first speed.

Clause 3. The apparatus of clause 2, wherein after pausing the knife for the predetermined amount of time and prior to advancing the knife at the second speed, the controller is configured to:
(i) communicate from the sensor a second force value exerted by the motor as the knife is contacting the ramp surface, and
(ii) determine whether the first force value exerted by the motor exceeds the first predetermined force threshold as the knife is contacting the ramp surface.

Clause 4. The apparatus of clause 1, wherein after advancing the knife at the second speed, the controller is configured to:
(i) obtain from the sensor a third force value exerted by the motor caused by tissue resistance on the knife while the knife is contacting the ramp surface,
(ii) determine whether the third force value of the motor exceeds the first predetermined force threshold, and
(iii) in response to determining the third force value of the motor exceeds the first predetermined force threshold, alter travel of the knife.

Clause 5. The apparatus of clause 4, wherein altering the travel of the knife in response to determining the third force value of the motor exceeds the first predetermined force threshold further comprises at least one of the following:
(A) pause the knife for a second predetermined amount of time,
(B) pause the knife until a third force value exerted by the motor is below the first predetermined force threshold, or
(C) advance the knife at a third speed, that is equal to or less than the second speed.

Clause 6. The apparatus of clause 1, wherein the controller is configured to, in response to the first force value exerted by the motor not reducing to below the first predetermined force threshold after a predetermined number of attempts, return the knife to a home position without the knife transitioning the first and second jaws to the closed position.

Clause 7. The apparatus of clause 1, wherein the sensor comprises a torque sensor configured to sense torque of the motor.

Clause 8. The apparatus of clause 1, further comprising a shaft assembly extending proximally from the end effector along a shaft axis, wherein the motor is coaxially positioned along the shaft axis.

Clause 9. The apparatus of clause 8, further comprising a housing extending proximally from the shaft assembly, wherein the motor and the sensor are positioned within the housing.

Clause 10. The apparatus of clause 1, wherein the controller is configured to increase the first predetermined force threshold as the knife moves distally along the ramp surface.

Clause 11. The apparatus of clause 1, wherein the knife is configured to pivot the second jaw relative to the first jaw as the knife moves distally along the ramp surface.

Clause 12. The apparatus of clause 1, wherein the second jaw includes a plurality of staple forming pockets, wherein the ramp surface is integrally formed together as a unitary piece together with the second jaw.

Clause 13. The apparatus of clause 1, wherein the ramp surface includes a concave portion and a convex portion, wherein the concave portion is proximal to the convex portion.

Clause 14. The apparatus of clause 1, wherein the knife includes a knife sled, wherein the knife sled includes at least one lateral wing configured to contact the ramp surface.

Clause 15. The apparatus of clause 1, wherein the knife includes a cutting surface, wherein the knife sled includes first and second lateral wings configured to contact the ramp surface, wherein the cutting surface is positioned between the first and second lateral wings.

Clause 16. An apparatus comprising:
(a) an end effector operable to clamp, staple, and cut tissue, comprising:
(i) a first jaw configured to selectively receive a staple cartridge,
(ii) a second jaw, wherein at least one of the first or second jaws includes a ramp surface, and
(iii) a knife configured to move relative to the first and second jaws, wherein the knife is configured to contact the ramp surface to transition the first and second jaws from an open position to a closed position;
(b) a motor configured to actuate the knife along a firing stroke while the staple cartridge is housed within the first jaw to thereby cut tissue clamped by the first and second jaws;
(c) a sensor configured to sense force exerted by the motor; and
(d) a controller in communication with the motor and the sensor, the controller being configured to:
(i) advance the knife along the ramp surface at a first speed,
(ii) communicate from the sensor a first force value exerted by the motor as the knife is contacting the ramp surface,
(iii) determine whether the first force value exerted by the motor exceeds a first predetermined force threshold, and
(iv) alter travel of the knife as the knife is contacting the ramp surface, by:
(A) pausing the knife for a predetermined amount of time, and
(B) after pausing the knife for a predetermined amount of time, advancing the knife at a second speed that is less than the first speed.

Clause 17. The apparatus of clause 16, wherein after pausing the knife for the predetermined amount of time and prior to advancing the knife at the second speed, the controller is configured to:
(i) communicate from the sensor a second force value exerted by the motor as the knife is contacting the ramp surface, and
(ii) determine whether the first force value exerted by the motor exceeds the first predetermined force threshold as the knife is contacting the ramp surface.

Clause 18. A method of operating a surgical instrument, wherein the surgical instrument includes an end effector operable to clamp, staple, and cut tissue, a motor, a sensor configured to sense force exerted by the motor, and a controller in communication with the motor and the sensor, wherein the end effector includes a first jaw configured to selectively receive a staple cartridge, a second jaw, and a knife configured to move relative to the first and second jaws, wherein at least one of the first or second jaws includes a ramp surface, the method comprising:
  (a) advancing the knife along the ramp surface at a first speed to transition the first and second jaws from an open position to a closed position;
  (b) obtaining, using the sensor, a first force value exerted by the motor as the knife is contacting the ramp surface;
  (c) communicating from the sensor a first force value exerted by the motor as the knife is contacting the ramp surface, wherein the motor is configured to actuate the knife along a firing stroke while the staple cartridge is housed within the first jaw to thereby cut tissue clamped by the first and second jaws;
  (d) determining whether the first force value exerted by the motor exceeds a first predetermined force threshold as the knife is contacting the ramp surface; and
  (e) in response to the determination, altering travel of the knife by at least one of the following:
    (i) pausing the knife for a predetermined amount of time,
    (ii) pausing the knife until a second force value exerted by the motor obtained from the sensor is below the first predetermined force threshold, or
    (iii) advancing the knife at a second speed that is less than the first speed.

Clause 19. The method of clause 18, wherein altering the travel of the knife comprises both:
  (i) pausing the knife for a predetermined amount of time, and
  (ii) after pausing the knife for the predetermined amount of time, advancing the knife at a second speed that is less than the first speed.

Clause 20. The method of clause 19, wherein after pausing the knife for the predetermined amount of time and prior to advancing the knife at the second speed, the method further comprising:
  (i) communicating from the sensor a second force value exerted by the motor as the knife is contacting the ramp surface, and
  (ii) determining whether the first force value exerted by the motor exceeds the first predetermined force threshold as the knife is contacting the ramp surface.

IV. MISCELLANEOUS

It should be understood that any one or more of the teachings, expressions, versions, examples, etc. described herein may be combined with any one or more of the other teachings, expressions, versions, examples, etc. that are described herein. The above-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
  (a) an end effector operable to clamp, staple, and cut tissue, comprising:
    (i) a first jaw configured to selectively receive a staple cartridge,
    (ii) a second jaw, wherein at least one of the first or second jaws includes a ramp surface, and
    (iii) a knife configured to move relative to the first and second jaws, wherein the knife is configured to contact the ramp surface to transition the first and second jaws from an open position to a closed position;

(b) a motor configured to actuate the knife along a firing stroke while the staple cartridge is housed within the first jaw to thereby cut tissue clamped by the first and second jaws;

(c) a sensor configured to sense force exerted by the motor; and (d) a controller in communication with the motor and the sensor, the controller configured to:

(i) advance the knife along the ramp surface at a first speed, (ii) obtain using the sensor a first force value exerted by the motor as the knife is contacting the ramp surface, (iii) determine whether the first force value exerted by the motor exceeds a first predetermined force threshold as the knife is contacting the ramp surface, and (iv) in response to determining the first force value exerted by the motor exceeds the first predetermined force threshold as the knife is contacting the ramp surface, altering travel of the knife by at least one of the following:

(A) pause the knife for a predetermined amount of time, (B) pause the knife until a second force value exerted by the motor obtained from the sensor is below the first predetermined force threshold, or (C) advance the knife at a second speed that is less than the first speed.

2. The apparatus of claim 1, wherein the controller is configured to alter the travel of the knife by both:

(A) pausing the knife for a predetermined amount of time, and (B) after pausing the knife for a predetermined amount of time, advancing the knife at a second speed that is less than the first speed.

3. The apparatus of claim 2, wherein after pausing the knife for the predetermined amount of time and prior to advancing the knife at the second speed, the controller is configured to:

(i) communicate from the sensor a second force value exerted by the motor as the knife is contacting the ramp surface, and (ii) determine whether the first force value exerted by the motor exceeds the first predetermined force threshold as the knife is contacting the ramp surface.

4. The apparatus of claim 1, wherein after advancing the knife at the second speed, the controller is configured to:

(i) obtain from the sensor a third force value exerted by the motor caused by tissue resistance on the knife while the knife is contacting the ramp surface, (ii) determine whether the third force value of the motor exceeds the first predetermined force threshold, and (iii) in response to determining the third force value of the motor exceeds the first predetermined force threshold, alter travel of the knife.

5. The apparatus of claim 4, wherein altering the travel of the knife in response to determining the third force value of the motor exceeds the first predetermined force threshold further comprises at least one of the following:

(A) pause the knife for a second predetermined amount of time, (B) pause the knife until a third force value exerted by the motor is below the first predetermined force threshold, or (C) advance the knife at a third speed, that is equal to or less than the second speed.

6. The apparatus of claim 1, wherein the controller is configured to, in response to the first force value exerted by the motor not reducing to below the first predetermined force threshold after a predetermined number of attempts, return the knife to a home position without the knife transitioning the first and second jaws to the closed position.

7. The apparatus of claim 1, wherein the sensor comprises a torque sensor configured to sense torque of the motor.

8. The apparatus of claim 1, further comprising a shaft assembly extending proximally from the end effector along a shaft axis, wherein the motor is coaxially positioned along the shaft axis.

9. The apparatus of claim 8, further comprising a housing extending proximally from the shaft assembly, wherein the motor and the sensor are positioned within the housing.

10. The apparatus of claim 1, wherein the controller is configured to increase the first predetermined force threshold as the knife moves distally along the ramp surface.

11. The apparatus of claim 1, wherein the knife is configured to pivot the second jaw relative to the first jaw as the knife moves distally along the ramp surface.

12. The apparatus of claim 1, wherein the second jaw includes a plurality of staple forming pockets, wherein the ramp surface is integrally formed together as a unitary piece together with the second jaw.

13. The apparatus of claim 1, wherein the ramp surface includes a concave portion and a convex portion, wherein the concave portion is proximal to the convex portion.

14. The apparatus of claim 1, wherein the knife includes a knife sled, wherein the knife sled includes at least one lateral wing configured to contact the ramp surface.

15. The apparatus of claim 1, wherein the knife includes a cutting surface, wherein the knife sled includes first and second lateral wings configured to contact the ramp surface, wherein the cutting surface is positioned between the first and second lateral wings.

16. An apparatus comprising:

(a) an end effector operable to clamp, staple, and cut tissue, comprising:

(i) a first jaw configured to selectively receive a staple cartridge, (ii) a second jaw, wherein at least one of the first or second jaws includes a ramp surface, and (iii) a knife configured to move relative to the first and second jaws, wherein the knife is configured to contact the ramp surface to transition the first and second jaws from an open position to a closed position;

(b) a motor configured to actuate the knife along a firing stroke while the staple cartridge is housed within the first jaw to thereby cut tissue clamped by the first and second jaws;

(c) a sensor configured to sense force exerted by the motor; and (d) a controller in communication with the motor and the sensor, the controller being configured to:

(i) advance the knife along the ramp surface at a first speed, (ii) communicate from the sensor a first force value exerted by the motor as the knife is contacting the ramp surface, (iii) determine whether the first force value exerted by the motor exceeds a first predetermined force threshold, and (iv) alter travel of the knife as the knife is contacting the ramp surface, by:
(A) pausing the knife for a predetermined amount of time, and
(B) after pausing the knife for a predetermined amount of time, advancing the knife at a second speed that is less than the first speed.

17. The apparatus of claim 16, wherein after pausing the knife for the predetermined amount of time and prior to advancing the knife at the second speed, the controller is configured to:
(i) communicate from the sensor a second force value exerted by the motor as the knife is contacting the ramp surface, and
(ii) determine whether the first force value exerted by the motor exceeds the first predetermined force threshold as the knife is contacting the ramp surface.

18. A method of operating a surgical instrument, wherein the surgical instrument includes an end effector operable to clamp, staple, and cut tissue, a motor, a sensor configured to sense force exerted by the motor, and a controller in communication with the motor and the sensor, wherein the end effector includes a first jaw configured to selectively receive a staple cartridge, a second jaw, and a knife configured to move relative to the first and second jaws, wherein at least one of the first or second jaws includes a ramp surface, the method comprising:
(a) advancing the knife along the ramp surface at a first speed to transition the first and second jaws from an open position to a closed position;
(b) obtaining, using the sensor, a first force value exerted by the motor as the knife is contacting the ramp surface;
(c) communicating from the sensor a first force value exerted by the motor as the knife is contacting the ramp surface, wherein the motor is configured to actuate the knife along a firing stroke while the staple cartridge is housed within the first jaw to thereby cut tissue clamped by the first and second jaws;
(d) determining whether the first force value exerted by the motor exceeds a first predetermined force threshold as the knife is contacting the ramp surface; and
(e) in response to the determination, altering travel of the knife by at least one of the following:
(i) pausing the knife for a predetermined amount of time,
(ii) pausing the knife until a second force value exerted by the motor obtained from the sensor is below the first predetermined force threshold, or
(iii) advancing the knife at a second speed that is less than the first speed.

19. The method of claim 18, wherein altering the travel of the knife comprises both:
(i) pausing the knife for a predetermined amount of time, and
(ii) after pausing the knife for the predetermined amount of time, advancing the knife at a second speed that is less than the first speed.

20. The method of claim 19, wherein after pausing the knife for the predetermined amount of time and prior to advancing the knife at the second speed, the method further comprising:
(i) communicating from the sensor a second force value exerted by the motor as the knife is contacting the ramp surface, and
(ii) determining whether the first force value exerted by the motor exceeds the first predetermined force threshold as the knife is contacting the ramp surface.

* * * * *